(12) United States Patent
Hellerbrand et al.

(10) Patent No.: US 7,763,270 B2
(45) Date of Patent: Jul. 27, 2010

(54) METAL IMPLANT COATED UNDER REDUCED OXYGEN CONCENTRATION WITH OSTEOINDUCTIVE PROTEIN

(75) Inventors: Klaus Hellerbrand, Geltendorf (DE); Nicola Beaucamp, Munich (DE); Ulrich Kohnert, Habach (DE)

(73) Assignee: Scil Technology GmbH (DE)

( * ) Notice: Subject to any disclaimer, the term of this patent is extended or adjusted under 35 U.S.C. 154(b) by 1274 days.

(21) Appl. No.: 10/527,047

(22) PCT Filed: Jul. 9, 2003

(86) PCT No.: PCT/EP03/07439

§ 371 (c)(1), (2), (4) Date: Nov. 15, 2005

(87) PCT Pub. No.: WO2004/024199

PCT Pub. Date: Mar. 25, 2004

(65) Prior Publication Data

US 2006/0240062 A1 Oct. 26, 2006

(30) Foreign Application Priority Data

Sep. 10, 2002 (EP) .................................. 02020403

(51) Int. Cl.
- A61F 2/00 (2006.01)
- A61K 33/00 (2006.01)
- A61K 33/24 (2006.01)

(52) U.S. Cl. .................. 424/423; 424/422; 424/600
(58) Field of Classification Search .............. 424/422, 424/423, 600
See application file for complete search history.

(56) References Cited

U.S. PATENT DOCUMENTS

| | | | |
|---|---|---|---|
| 4,596,574 A | 6/1986 | Urist | |
| 4,877,864 A | 10/1989 | Wang et al. | |
| 4,975,526 A | 12/1990 | Kuberasampath et al. | |
| 5,011,691 A | 4/1991 | Oppermann et al. | |
| 5,013,649 A | 5/1991 | Wang et al. | |
| 5,106,748 A | 4/1992 | Wozney et al. | |
| 5,108,436 A | 4/1992 | Chu et al. | |
| 5,108,922 A | 4/1992 | Wang et al. | |
| 5,116,738 A | 5/1992 | Wang et al. | |
| 5,141,905 A | 8/1992 | Rosen et al. | |
| 5,158,934 A | 10/1992 | Ammann et al. | |
| 5,162,114 A | 11/1992 | Kuberasampath et al. | |
| 5,166,058 A | 11/1992 | Wang et al. | |
| 5,171,574 A | 12/1992 | Kuberasampath et al. | |
| 5,177,406 A | 1/1993 | Troxell | |
| 5,187,076 A | 2/1993 | Wozney et al. | |
| 5,207,710 A | 5/1993 | Chu et al. | |
| 5,258,029 A | * 11/1993 | Chu et al. ................. | 623/23.61 |
| 5,258,494 A | 11/1993 | Oppermann et al. | |
| 5,266,683 A | 11/1993 | Oppermann et al. | |
| 5,290,763 A | 3/1994 | Poser et al. | |
| 5,324,819 A | 6/1994 | Oppermann et al. | |
| 5,344,654 A | 9/1994 | Rueger et al. | |
| 5,354,557 A | 10/1994 | Oppermann et al. | |
| 5,366,875 A | 11/1994 | Wozney et al. | |
| 5,371,191 A | 12/1994 | Poser et al. | |
| 5,385,887 A | 1/1995 | Yim et al. | |
| 5,397,235 A | 3/1995 | Elia | |
| 5,409,896 A | 4/1995 | Ammann et al. | |
| 5,422,340 A | 6/1995 | Ammann et al. | |
| 5,458,653 A | 10/1995 | Davidson | |
| 5,459,047 A | 10/1995 | Wozney et al. | |
| 5,464,440 A | 11/1995 | Johansson | |
| 5,468,845 A | 11/1995 | Oppermann et al. | |
| 5,543,394 A | 8/1996 | Wozney et al. | |
| 5,563,124 A | 10/1996 | Damien et al. | |
| 5,604,204 A | 2/1997 | Ammann et al. | |
| 5,607,474 A | 3/1997 | Athanasiou et al. | |
| 5,610,021 A | 3/1997 | Rueger et al. | |
| 5,618,924 A | 4/1997 | Wang et al. | |
| 5,631,142 A | 5/1997 | Wang et al. | |
| 5,635,372 A | 6/1997 | Celeste et al. | |
| 5,635,373 A | 6/1997 | Wozney et al. | |
| 5,650,176 A | 7/1997 | Lee et al. | |
| 5,650,276 A | 7/1997 | Smart et al. | |
| 5,652,118 A | 7/1997 | Ozkaynak et al. | |
| 5,652,337 A | 7/1997 | Oppermann et al. | |
| 5,656,593 A | 8/1997 | Kuberasampath et al. | |
| 5,658,882 A | 8/1997 | Celeste et al. | |
| 5,670,336 A | 9/1997 | Oppermann et al. | |
| 5,674,844 A | 10/1997 | Kuberasampath et al. | |

(Continued)

FOREIGN PATENT DOCUMENTS

DE 196 47 853 5/1998

(Continued)

OTHER PUBLICATIONS

Weng et al., "Bone Regeneration around Implants with Bone Growth Factor rhGDF-5", *J. Dent. Res.*, 2003; 82 (Special Issue b): 377, Abstract # 2943.

(Continued)

*Primary Examiner*—Ruth A Davis
(74) *Attorney, Agent, or Firm*—Pillsbury Winthrop Shaw Pittman LLP

(57) ABSTRACT

The present invention relates to a method for producing a device comprising the steps of (a) providing a solution comprising dissolved osteoinductive protein, (b) contacting the solution of the preceding step with a carrier containing a surface of metal or a metal alloy, (c) allowing coating of the surface of said carrier with said dissolved protein and (d) drying of the coated carrier obtained in step (c) wherein steps (b) to (d) are carried out under a reduced concentration of oxygen. The invention also encompasses a device obtainable by the method of the present invention. Moreover, the present invention relates to a pharmaceutical composition comprising the said device and to the use of the device for the preparation of a pharmaceutical composition to be used for an accelerated osseointegration and new bone formation. Finally, the present invention relates to a kit comprising the device of the present invention.

27 Claims, 10 Drawing Sheets

U.S. PATENT DOCUMENTS

Figure 1:
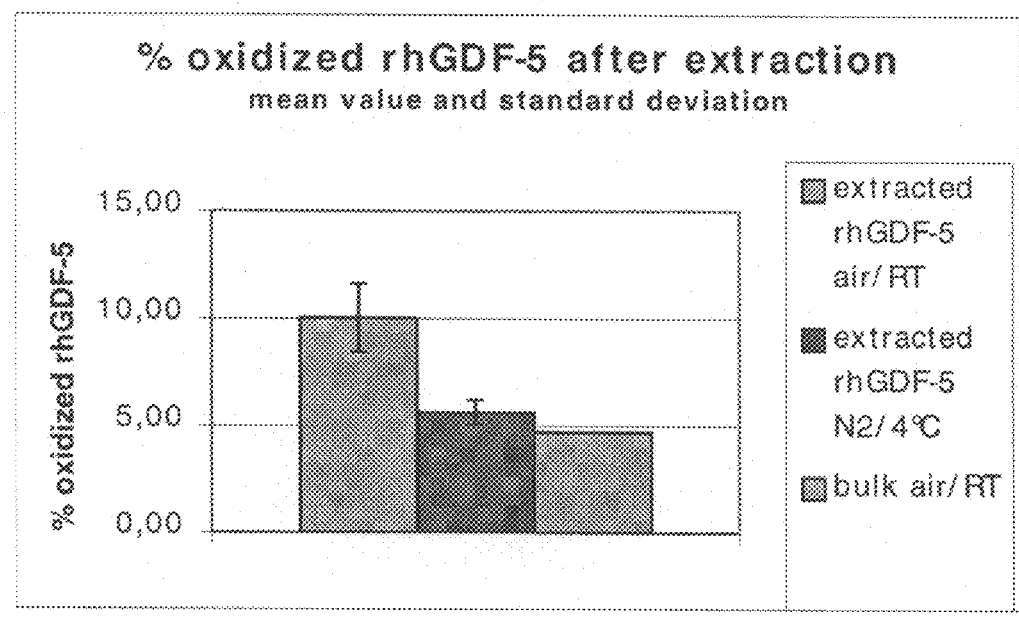

| | | | |
|---|---|---|---|
| 5,676,976 A | 10/1997 | Lee et al. |
| 5,681,746 A | 10/1997 | Bodner et al. |
| 5,683,461 A | 11/1997 | Lee et al. |
| 5,707,810 A | 1/1998 | Smart et al. |
| 5,714,589 A | 2/1998 | Oppermann et al. |
| 5,728,679 A | 3/1998 | Celeste et al. |
| 5,733,878 A | 3/1998 | Kuberasampath et al. |
| 5,739,107 A | 4/1998 | Cohen et al. |
| 5,741,641 A | 4/1998 | Smart et al. |
| 5,750,651 A | 5/1998 | Oppermann et al. |
| 5,801,014 A | 9/1998 | Lee et al. |
| 5,814,604 A | 9/1998 | Oppermann et al. |
| 5,834,179 A | 11/1998 | Jones et al. |
| 5,849,686 A | 12/1998 | Kuberasampath et al. |
| 5,849,880 A | 12/1998 | Wozney et al. |
| 5,854,071 A | 12/1998 | Oppermenn et al. |
| 5,863,758 A | 1/1999 | Oppermann et al. |
| 5,876,452 A | 3/1999 | Athanasiou et al. |
| 5,939,388 A | 8/1999 | Rosen et al. |
| 5,958,441 A | 9/1999 | Oppermann et al. |
| 5,972,884 A | 10/1999 | Cohen et al. |
| 5,994,131 A | 11/1999 | Smart et al. |
| 6,013,517 A | 1/2000 | Respess et al. |
| 6,013,853 A | 1/2000 | Athanasiou et al. |
| 6,022,853 A | 2/2000 | Kuberasampath et al. |
| 6,027,742 A | 2/2000 | Lee et al. |
| 6,027,919 A | 2/2000 | Celeste et al. |
| 6,034,229 A | 3/2000 | Celeste et al. |
| 6,069,295 A | 5/2000 | Leitao |
| 6,071,695 A | 6/2000 | Ozkaynak et al. |
| 6,071,708 A | 6/2000 | Jones et al. |
| 6,077,823 A | 6/2000 | Kuberasampath et al. |
| 6,090,776 A | 7/2000 | Kuberasampath et al. |
| 6,117,456 A | 9/2000 | Lee et al. |
| 6,118,043 A | 9/2000 | Nies et al. |
| 6,120,760 A | 9/2000 | Hötten et al. |
| 6,129,928 A | 10/2000 | Sarangapani et al. |
| 6,132,463 A | 10/2000 | Lee et al. |
| 6,136,369 A | 10/2000 | Leitao et al. |
| 6,139,578 A | 10/2000 | Lee et al. |
| 6,143,948 A | 11/2000 | Leitao et al. |
| 6,146,686 A | 11/2000 | Leitao |
| 6,150,328 A | 11/2000 | Wang et al. |
| 6,153,583 A | 11/2000 | Oppermann et al. |
| 6,177,406 B1 | 1/2001 | Wang et al. |
| 6,187,742 B1 | 2/2001 | Wozney et al. |
| 6,194,376 B1 | 2/2001 | Kuberasampath et al. |
| 6,197,550 B1 | 3/2001 | Hötten et al. |
| 6,207,813 B1 | 3/2001 | Wozney et al. |
| 6,211,146 B1 | 4/2001 | Kuberasampath et al. |
| 6,214,368 B1 | 4/2001 | Lee et al. |
| 6,245,889 B1 | 6/2001 | Wang et al. |
| 6,245,896 B1 | 6/2001 | Lee et al. |
| 6,261,322 B1 | 7/2001 | Despres, III et al. |
| 6,261,835 B1 | 7/2001 | Oppermann et al. |
| 6,277,151 B1 | 8/2001 | Lee et al. |
| 6,284,872 B1 | 9/2001 | Celeste et al. |
| 6,287,341 B1 | 9/2001 | Lee et al. |
| 6,288,031 B1 | 9/2001 | Kuberasampath et al. |
| 6,297,213 B1 | 10/2001 | Oppermann et al. |
| 6,328,765 B1 | 12/2001 | Hardwick et al. |
| 6,331,312 B1 | 12/2001 | Lee et al. |
| 6,333,312 B1 | 12/2001 | Kuberasampath et al. |
| 6,344,061 B1 | 2/2002 | Leitao et al. |
| 6,365,150 B1 | 4/2002 | Leboulch et al. |
| 6,395,883 B1 | 5/2002 | Jones et al. |
| 6,399,569 B1 | 6/2002 | Cohen et al. |
| 6,423,544 B1 | 7/2002 | Hardy |
| 6,432,919 B1 | 8/2002 | Wang et al. |
| 6,495,513 B1 | 12/2002 | Rueger et al. |
| 6,506,729 B1 | 1/2003 | Rueger et al. |
| 6,531,445 B1 | 3/2003 | Cohen et al. |
| 6,533,821 B1 | 3/2003 | Lally |
| 6,541,037 B1 | 4/2003 | Lee et al. |
| 6,544,290 B1 | 4/2003 | Lee et al. |
| 6,551,995 B1 | 4/2003 | Oppermann et al. |
| 6,555,107 B2 | 4/2003 | Poeschla et al. |
| 6,565,843 B1 | 5/2003 | Cohen et al. |
| 6,586,388 B2 | 7/2003 | Oppermann et al. |
| 6,613,744 B2 | 9/2003 | Wozney et al. |
| 6,730,297 B1 | 5/2004 | Davidson et al. |
| 2001/0016347 A1 | 8/2001 | Poeschla et al. |
| 2002/0009822 A1 | 1/2002 | Park |
| 2002/0016635 A1 | 2/2002 | Despres, III et al. |
| 2002/0037281 A1 | 3/2002 | Davidson et al. |
| 2002/0048805 A1 | 4/2002 | Johnston et al. |
| 2002/0049159 A1 | 4/2002 | Rueger et al. |
| 2002/0068354 A1 | 6/2002 | Johnston et al. |
| 2002/0082224 A1 | 6/2002 | Jolly et al. |
| 2002/0082679 A1 | 6/2002 | Sirhan et al. |
| 2002/0082694 A1 | 6/2002 | McKay |
| 2002/0136692 A1 | 9/2002 | Haroon et al. |
| 2002/0155137 A1 | 10/2002 | Lee et al. |
| 2002/0155167 A1 | 10/2002 | Lee et al. |
| 2002/0160494 A1 | 10/2002 | Celeste et al. |
| 2002/0165361 A1 | 11/2002 | Lee et al. |
| 2002/0169066 A1 | 11/2002 | Cassidy et al. |
| 2003/0003565 A1 | 1/2003 | Dubensky, Jr. et al. |
| 2003/0009225 A1 | 1/2003 | Khandkar et al. |
| 2003/0032586 A1 | 2/2003 | Rueger et al. |
| 2003/0039636 A1 | 2/2003 | Leboulch et al. |
| 2003/0044596 A1 | 3/2003 | Lazarov et al. |
| 2003/0049328 A1 | 3/2003 | Dalal et al. |
| 2003/0049329 A1 | 3/2003 | Lee et al. |
| 2003/0069401 A1 | 4/2003 | Oppermann et al. |
| 2003/0082232 A1 | 5/2003 | Lee et al. |
| 2003/0104611 A1 | 6/2003 | Johnston et al. |
| 2003/0104993 A1 | 6/2003 | Rueger et al. |
| 2003/0105004 A1 | 6/2003 | Jones et al. |
| 2003/0109445 A1 | 6/2003 | Rueger et al. |
| 2003/0124169 A1 | 7/2003 | Oppermann et al. |
| 2003/0125230 A1 | 7/2003 | Cohen et al. |
| 2003/0180376 A1 | 9/2003 | Dalal et al. |
| 2005/0002907 A1 | 1/2005 | Mitrophanous et al. |

FOREIGN PATENT DOCUMENTS

| | | | |
|---|---|---|---|
| EP | 0 135 083 A2 | 7/1984 |
| EP | 0 361 896 A2 | 4/1990 |
| EP | 0 411 105 B1 | 6/1995 |
| EP | 0 688 869 A1 | 12/1995 |
| EP | 0 688 869 B1 | 12/1995 |
| EP | 0 362 367 B1 | 2/1996 |
| EP | 0 723 013 A2 | 7/1996 |
| EP | 0 723 013 A3 | 7/1996 |
| EP | 0 723 013 B1 | 7/1996 |
| EP | 0 313 578 B1 | 8/1996 |
| EP | 0 372 031 B1 | 9/1996 |
| EP | 0 625 891 B1 | 1/1997 |
| EP | 0 679 097 B1 | 5/1997 |
| EP | 0 806 212 A1 | 11/1997 |
| EP | 0 429 570 B1 | 1/1998 |
| EP | 0 448 704 B1 | 6/1998 |
| EP | 0 643 767 B1 | 7/1998 |
| EP | 0 584 283 B1 | 12/1999 |
| EP | 0 623 031 B1 | 2/2000 |
| EP | 0 601 106 B1 | 5/2000 |
| EP | 0 601 106 B2 | 5/2000 |
| EP | 0 812 207 B1 | 11/2000 |
| EP | 0 575 555 B1 | 8/2001 |
| EP | 1 221 484 A2 | 7/2002 |
| EP | 1 221 484 A3 | 7/2002 |
| EP | 1 225 225 A2 | 7/2002 |
| EP | 1 225 225 A3 | 7/2002 |

| | | |
|---|---|---|
| EP | 0 806 211 B1 | 10/2002 |
| EP | 1 254 956 A2 | 11/2002 |
| EP | 1 254 956 A3 | 11/2002 |
| EP | 0 714 665 B1 | 1/2003 |
| EP | 0 806 212 B1 | 4/2003 |
| EP | 1 150 726 B1 | 11/2003 |
| EP | 0 936 929 B1 | 6/2004 |
| EP | 1 223 990 B1 | 7/2004 |
| EP | 0 729 325 B1 | 11/2004 |
| JP | 2001-50597 | 4/2001 |
| JP | 2001-511042 | 8/2001 |
| WO | 88/00205 A1 | 1/1988 |
| WO | 90/11366 A1 | 10/1990 |
| WO | 91/11148 A1 | 8/1991 |
| WO | 93/05751 A2 | 4/1993 |
| WO | 93/16099 A2 | 8/1993 |
| WO | 93/25246 A1 | 12/1993 |
| WO | 94/15653 | 7/1994 |
| WO | 94/15949 A1 | 7/1994 |
| WO | 95/01760 A2 | 1/1995 |
| WO | 95/01760 A3 | 1/1995 |
| WO | 95/13767 A1 | 5/1995 |
| WO | 95/16035 A2 | 6/1995 |
| WO | 95/16035 A3 | 6/1995 |
| WO | 96/36562 A1 | 11/1996 |
| WO | 97/31661 | 9/1997 |
| WO | WO98/16268 A2 | 4/1998 |
| WO | WO98/16268 A3 | 4/1998 |
| WO | 98/21972 A2 | 5/1998 |
| WO | 98/21972 A3 | 5/1998 |
| WO | 98/33514 A1 | 8/1998 |
| WO | 98/34655 | 8/1998 |
| WO | 98/40113 A1 | 9/1998 |
| WO | 98/51354 | 11/1998 |
| WO | 99/11202 A1 | 3/1999 |
| WO | 99/58167 A1 | 11/1999 |
| WO | 00/45870 A1 | 8/2000 |
| WO | 00/45871 A1 | 8/2000 |
| WO | 00/72775 A1 | 12/2000 |
| WO | 00/72776 A1 | 12/2000 |
| WO | 00/72777 A1 | 12/2000 |
| WO | WO 00/72777 | 12/2000 |
| WO | 01/28602 A1 | 4/2001 |
| WO | 01/28603 A1 | 4/2001 |
| WO | 01/28605 A1 | 4/2001 |
| WO | 0197679 A2 | 12/2001 |
| WO | 02/40074 A1 | 5/2002 |
| WO | WO 02/45764 | 6/2002 |
| WO | 02/070029 A2 | 9/2002 |
| WO | 02/070029 A3 | 9/2002 |
| WO | 02/083188 A2 | 10/2002 |
| WO | 03/003937 A1 | 1/2003 |
| WO | 03/003939 A1 | 1/2003 |
| WO | 03/059407 A1 | 7/2003 |

OTHER PUBLICATIONS

Ludwig et al., "GDF-5 coated beta-TCP in sinus augmentation in minipigs", Int. J. Oral Maxillofac. Surg., 2003; 32 (Supplement 1): S55, Abstract O26.9.

Wolfman et al., "Ectopic Induction of Tendon and Ligament in Rats by Growth and Differentiation Factors 5, 6, and 7, Members of the TGF-β Gene Family", J. Clin. Invest., 1997;.100(2): 321-330.

GenBank Accession No. NP_00548, (GI:4503969). Growth differentiation factor 5 preproprotein; cartilage-derived morphogenetic protein-1 [Homo sapiens]. Last modified Dec. 20, 2003.

GenBank Accession No. P43026 (GI:20141384). Growth/differentiation factor 5 precursor (GDF-5); cartilage-derived morphogenetic protein 1 (CDMP-1). Last modified Jun. 15, 2004.

GenBank Accession No. JC2347 (GI:631181). Growth/differentiation factor 5-human. Last modified Mar. 17, 2000.

GenBank Accession No. CAA56874 (GI:671525). Gdf5 [Homo sapiens]. Last modified Feb. 24, 1995.

GenBank Accession No. AAH32495 (GI:22749747). GDF5 protein [Homo sapiens]. Last modified Oct. 7, 2003.

GenBank Accession No. CAB89416 (GI:7671666). Growth differentiation factor 5; cartilage-derived morphogenetic protein-1 [Homo sapiens]. Last modified Apr. 11, 2001.

Alam et al.; Evaluation of ceramics composed of different hydroxyapatite to tricalcium phosphate ratios as carriers for rhBMP-2; Bionmaterials vol. 22; 2001; p. 1643-1651.

Ripamonti, U., et al., Induction of Bone Formation by Recombinant Human Osteogenic Protein-1 and Sintered Porous Hydroxyapatite in Adult Primates, Plast. Reconstr. Surg. 107:977-988 (2001).

Celeste, A.J., et al., Identification Of Transforming Growth Factor Beta Family Members Present in Bone-Inductive Protein Purified From Bovine Bone, Proc. Natl. Acad. Sci. U.S.A, 87(24):9843-9847 (1990).

Chang, S.C., et al., Cartilage-Derived Morphogenetic Proteins. New Members Of The Transforming Growth Factor-Beta Superfamily Predominantly Expressed In Long Bones During Human Embryonic Development, J. Biol. Chem. 269(45):28227-2823 (1994).

EMEA. ICH Topic Q 3 C—Impurities: Residual Solvents. 1-19. 1997. Ref Type: Generic.

Friess,W., et al., Bone Regeneration With Recombinant Human Bone Morphogenetic Protein-2 (Rhbmp-2) Using Absorbable Collagen Sponges (ACS): Influence Of Processing On ACS Characteristics And Formulation, Pharm. Dev. Technol. 4(3):387-96 (1999).

Gao,T., et al., Composites of Bone Morphogenetic Protein (BMP) And Type IV Collagen, Coral-Derived Coral Hydroxyapatite, And Tricalcium Phosphate Ceramics, Int. Orthop., 20(5):321-325 (1996).

Gombotz,W.R., et al., Stability, Characterization, Formulation, And Delivery System Development For Transforming Growth Factor-Beta 1. In Formulation, Characterization, and Stability of Protein Drugs New York and London, 1996; vol. 9, 219-45.

Griffith,D.L., et al., Three-Dimensional Structure Of Recombinant Human Osteogenic Protein 1: Structural Paradigm For The Transforming Growth Factor Beta Superfamily, Proc Natl Acad Sci U.S.A., 93(2):878-883 (1996).

Hotten,G., et al., Cloning And Expression Of Recombinant Human Growth/Differentiation Factor 5, Biochem. Biophys. Res. Commun., 204(2):646-652 (1994).

Hotz,G., et al., Bone Substitute With Osteoinductive Biomaterials—Current And Future Clinical Applications, Int. J. Oral Maxillofac. Surg., 23(6 Pt 2):413-417 (1994).

Katagiri,T., et al., The Non-Osteogenic Mouse Pluripotent Cell Line, C3H10T1/2, Is Induced To Differentiate Into Osteoblastic Cells By Recombinant Human Bone Morphogenetic Protein-2., Biochem. Biophys. Res. Commun., 172(1):295-299 (1990).

Lind, M., et al., Transforming Growth Factor-Beta 1 Enhances Bone Healing To Unloaded Tricalcium Phosphate Coated Implants: An Experimental Study In Dogs, J. Orthop. Res., 14(3):343-350 (1996).

Lind,M., Growth Factors: Possible New Clinical Tools. A Review, Acta. Orthop. Scand., 67(4):407-17 (1996).

Nishitoh, H., et al., Identification Of Type I And Type II Serine/Threonine Kinase Receptors For Growth/Differentiation Factor-5, J. Biol. Chem., 271(35):21345-21352 (1996).

Ozkaynak, E., et al., OP-1 cDNA Encodes An Osteogenic Protein In The TGF-Beta Family, The Embo. J., 9(7):2085-2093 (1990).

Scheufler, C., et al., Crystal StructureOf Human Bone Morphogenetic Protein-2 At 2.7 A Resolution, J. Mol. Biol., 287(1):103-115 (1999).

Schmitt, J., et al., Bone Morphogenetic Proteins: An Update On Basic Biology And Clinical Relevance, J. Orthop. Res., 17:269-278 (1999).

Spiro, R.C., et al., Spinal Fusion With Recombinant Human Growth And Differentiation Factor-5 Combined With A Mineralized Collagen Matrix, The Anatomical Record, 263:388-395 (2001).

Storm, E.E., et al., GDF5 Coordinates Bone And Joint Formation During Digit Development, Dev Biol, 209 (1), 11-27 (1999).

Terheyden, H., et al., Recombinant Human Osteogenic Protein 1 In The Rat Mandibular Augmentation Model: Differences In Morphology Of The Newly Formed Bone Are Dependent On The Type Of Carrier, Mund Kiefer Gesichtschir., 1:272-275 (1997).

Wozney, J.M., et al., Bone Morphogenetic Protein And Bone Morphogenetic Protein Gene Family in Bone Formation and Repair, Clin. Orthop, 346:26-37 (1998).

Wozney, J.M., et al., Novel Regulators Of Bone Formation: Molecular Clones And activities. Science, 242(4885):1528-1534 (1988).

Baldwin, R.L., et al., How Hofmeister Ion Interactions Affect Protein Stability, *Biophysical Journal*, 71:2056-2063 (1996).

US 5,182,365, 01/1993, Oppermann et al. (withdrawn)

* cited by examiner

METAL IMPLANT COATED UNDER REDUCED OXYGEN CONCENTRATION WITH OSTEOINDUCTIVE PROTEIN

The present invention relates to a method for producing a device comprising the steps of (a) providing a solution comprising dissolved osteoinductive protein, (b) contacting the solution of the preceding step with a carrier containing a surface of metal or a metal alloy, (c) allowing coating of the surface of said carrier with said dissolved protein and (d) drying of the coated carrier obtained in step (c) wherein steps (b) to (d) are carried out under a reduced concentration of oxygen. The invention also encompasses a device obtainable by the method of the present invention. Moreover, the present invention relates to a pharmaceutical composition comprising the said device and to the use of the device for the preparation of a pharmaceutical composition to be used for an accelerated osseointegration and new bone formation. Finally, the present invention relates to a kit comprising the device of the present invention.

During the last decades, many methods were described to improve the quality of implants concerning the bone implant contact and their biocompatibility. The demands for implants are extreme as such devices have to be rigidly fixed to the bone and be stable to e.g. high pressure (e.g. teeth, joints). The initial tissue response after implantation is dependent on the presence of specific growth factors released from the surrounding tissues that stimulate cell growth and differentiation.

Although there are well established fixation methods for dental implants there is still a tendency for them to loosen with time. A variety of approaches have been described in order to improve the incorporation of the respective implant (osseointegration). These approaches include the coating of implants of different sources (e.g. ceramic, metal or others, see EP-B1 0 657 146) with biodegradable materials (e.g. tri-calcium phosphate, hydroxyapatite) and various methods for the etching of metal surfaces. Surface irregularities in the nanometer and micrometer range are assumed to improve the collagen and cell ingrowth (T. Albrektsson in: Handbook of Biomaterials (Black, J and Hastings, G (eds.), Chapman & Hall, London, 1998, pp 500-512).

Coating of metal implants with ceramic surfaces is described as e.g. the mixture of two powders, one metal powder and one powder containing calcium phosphate (EP 0467948) processed to implant material during a sintering process.

A variety of other sintering methods are described to manufacture composite ceramic material (Offenlegungsschrift DE 2928007, U.S. Pat. No. 4,882,196). A main focus is laid on the coating of metal surfaces with calcium phosphates like tri-calcium phosphate or hydroxyapatite (Y. Tsui, 1998) which allow an improved incorporation of the implants (U.S. Pat. No. 6,312,472; US-Application A-20020038149). The described calcium phosphates and a variety of other inorganic biocompatible materials have the characteristic to form pores. These pores are said to enhance the incorporation of the implant into the native bone (WO 00/72776; U.S. Pat. No. 4,051,598; EP 0806211, H. Jennissen, 2001) as the native bone is growing into the pores at the same time biodegrading the inorganic calcium phosphate layer of the implant (WO 96/10370; WO 01/97679). Besides the composite material implants are described consisting of layers, where the lower layer of the implant, often comprising metal or alloys like titanium or titanium alloy (WO 98/43550; WO 00/72777) is coated with a layer of the calcium phosphates (EP 0478532). Typically the coating with calcium phosphates is achieved by hydrothermal treatment (EP 0548365) or by soaking and precipitation (U.S. Pat. No. 6,129,928, WO 97/41273) or plasma spraying (U.S. Pat. Nos. 5,697,997, 6,113,993, EP 0548365, EP 0739191, Lichtinger, 2001).

The layer of calcium phosphate on the main body of the implant can be part of either a mixture of materials within one layer (WO 98/48862, U.S. Pat. No. 5,934,287; US-Application A-20020033548) or a multilayer formation (WO 02/09788, U.S. Pat. No. 6,322,728).

Besides to the modifications of the surface several methods are described in which proteins or protein mixtures (mainly growth factors) are coated onto orthopaedic or dental implants. These proteins are said to significantly accelerate the incorporation of implants (Lichtinger, 2001; Shah, 1999). Several methods are described for the direct coating of proteins onto the metal surfaces. However, these methods have several disadvantages, especially the rapid release of proteins from the metal surface which does not allow to maintain the protein for the time interval necessary for the induction of bone formation (Lichtinger, 2001).

In order to avoid the rapid release (spontaneous burst) of the protein K. Endo (1995) and Voggenreiter et al. (2001) describe the immobilisation of the proteins by covalent binding to the metal surface. The activity of the respective proteins is maintained. However, the covalent binding may induce structural changes which have impact on the immunogenicity of proteins.

Many researchers have stated that successful implantation of the osteogenic factors for endochondral bone formation requires that the proteins are associated with a suitable carrier material or matrix which maintains the proteins at the site of application (U.S. Pat. No. 5,344,654). In order to overcome these difficulties U.S. Pat. No. 5,258,029 teaches "the osteogenic protein of the invention will normally be formulated in osteogenically effective amounts with pharmaceutically acceptable solid or fluid carriers. Preferably, the formulations include a matrix that is capable of providing a structure for developing bone and cartilage. Potential matrices may be biodegradable or nonbiodegradable, and may be chemically or biologically defined". The suspension of the TGF-$\beta$-protein and the carrier is dried and subsequently applied to the load carrying prosthetic. Disadvantages of these methods are the use of animal derived collagens or inorganic components which may be abraded during implantation.

A further method to overcome the quick outwash of the protein is described by Lichtinger et al. (2001) who treat the titanium alloy surface with chromosulfuric acid in order to achieve an ultrahydrophilic bioadhesive surfaces. However, chromosulfuric acid should be avoided during the manufacture of medicinal products or medical devices as residual amounts of such acid remaining on the surface may cause oxidation of the protein with subsequent structural and functional changes and also may cause harm to the patient.

Further methods are described in WO 00/72777 and WO 00/72778 which use a depot which is formed by a pore arrangement of a thick oxide layer on the titanium surface or by internal spaces, channels or recesses. However, it is well known that proteins tend to become oxidized in the presence of metals and metal ions (Li et al. (1997), Ann. Occup. Hyg. 41, suppl. 1, 379-383). Thus, a drawback of the aforementioned devices may be that the proteins are oxidized on the surfaces of the implants. The oxidation may result in structural changes which can result in the formation of immunogenic reactions.

Thus, the technical problem underlying the present invention is to provide means for improved bone augmentation.

This technical problem is solved by the embodiments characterized in the claims.

Accordingly, the present invention relates to a method for the production of a device comprising the steps of:
(a) providing a solution comprising dissolved osteoinductive protein;
(b) contacting the solution of step (a) with a carrier containing a surface of metal or a metal alloy;
(c) allowing coating of the surface of said carrier with said dissolved protein; and
(d) drying of the coated carrier obtained in step (c),
wherein steps (b) to (d) are carried out under a reduced concentration of oxygen.

The term "producing" encompasses in addition to the steps explicitly mentioned further steps of manufacturing, such as packaging etc. Preferably, the method of the present invention is carried out as an automated manufacturing method assisted by suitable robots. The terms "producing" and "manufacturing" are interchangeable in the sense of this invention.

The term "device" as used in accordance to the present invention refers to a entity which comprises at least two components. One of said components is a carrier. Carriers which can be used within the meaning of the present invention include solid carriers, such as full metal or alloy carriers, and metal or alloy matrices. In addition the present invention encompasses solid carriers which comprise hollow spaces and cavities. Moreover, said carrier, preferably, has an enlarged surface due to formation of macro- and micro-pores. Preferably, said macro- or micro-pores are restricted to the surface layer of the carrier. Also encompassed by the present invention are carriers which consist of at least two different components, wherein a metal or alloy component is used as core or core layer and, e.g. a ceramic material is used as surface layer. The carrier surface has a high affinity for osteoinductive proteins but nevertheless allows release of said proteins in vivo. In accordance with the present invention, said carrier is, preferably, a metal or alloy described infra. The carrier comprised by the device of the invention may be brought into a suitable form for administration of the device in vivo. This also encompasses the formation of implants or entire chirurgic prostheses. These prostheses are, preferably, formed from or coated with metallic surfaces as will be described in more detail below. Prostheses are made from titan or titanium alloys like titan alloy or stainless steel.

Another component of said device is a protein or polypeptide which has osteoinductive properties as will be explained in detail below. The protein or polypeptide is immobilized on the surface of the carrier. It is preferred that the binding of said protein or polypeptide to the carrier is reversible. Hence, it is envisaged that the protein or polypeptide which has osteoinductive properties is not coupled to the metallic surface of the carrier by means of covalent bonding. Preferably, coupling occurs via electrostatic interactions, hydrophobic or non-electrostatic interactions, such as Van-der-Waals forces. Due to the reversible binding of the osteoinductive protein, dissolution of said protein is allowed once the device has been brought into a suitable in vivo surrounding, such as a bone cavity. Preferably, said dissolution of the proteins is slow release allowing diffusion of the protein into the tissue which surrounds the device. Thus, as demonstrated in the appended examples, the device allows the local presence of osteoinductive and native proteins which accelerate the formation of new bone and the ingrowth of the bone into the surface of the matrix. The device of the invention may be an implant which means that the terms "device" and "implant" as used herein are interchangeable. It is well-known that the term "implant" refers to every device as provided by the instant invention which is designed to be brought totally or partially underneath the epithelial surface (Koeck, B. and Wagner, W. (Eds.) 1996). The implant may be flat, dense or of a complex shape, i.e. any conventionally used or operable device can be used The above-mentioned implants range from a simple cylindrical shape as used e.g. for replacement of long bones or as a basis for artificial teeth, to flat implants as used for replacement of cephalic flat bones and artificial joints like hip, knee or elbow.

The coating of the device of the invention with the osteoinductive protein is intended to initiate and stimulate the transformation of mesenchymal stem cells into osteoblasts and chondrocytes as will be described below. Accordingly it is envisaged that only those parts of the device of the invention need to be coated, which are directed towards the respective bone tissue. Said part is preferably the entire surface or at least the parts thereof which are juxtaposed to the bone tissue. For example, a dental implant which is used to replace a missing tooth comprises a threaded part which is screwed into the jaw bone and an extended part (socket) which is used for anchoring an artificial tooth crown. Accordingly, it is only necessary to coat the threaded part with the osteoinductive protein. However, the part which is not coated with the osteoinductive protein may be coated with other agents which, such as calcium phosphates, collagen or similar agents.

The term "osteoinductive" refers to the capability of the transformation of mesenchymal stem cells and pre-osteoblasts into osteoblasts. A prerequisite for osteoinduction is a signal which is distributed by the device into the surrounding tissues where the aforementioned osteoblast precursors and other mesenchymal cells become activated. Osteoinduction as used herein encompasses the differentiation of mesenchymal cells into the bone precursor cells, the ostelasts. Moreover, osteoinduction also comprises the differentiation of said osteoblasts into osteocytes, the mature cells of the bone. Thus, osteoinduction requires differentiation of undifferentiated or less-differentiated cells into osteocytes which are capable of forming the bone. As has been described above, the osteoinductive proteins used in accordance with the present invention are slowly released from the device after implantation and are distributed efficiently in the surrounding tissues. Moreover, the proteins and polypeptides encompassed by the present invention have osteoinductive properties in vivo. For example, it is well known in the art that the Transforming Growth Factor-β (TGF-β) superfamily encompasses members which have osteoinductive properties. Individual members of said TGF-β superfamily which have particular well osteoinductive properties are listed infra. In conclusion, the osteoinductive proteins of the device of the present invention on the surface and after having been released from the carrier will serve as a osteoinductive signal for the osteocyte precursors of the tissue surrounding the side of implantation of the device.

The term "osteoinductive protein" or as set forth above, refers to Transforming Growth Factor-β (TGF-β) superfamily members which have osteoinductive properties, such as Growth and Differentiation Factor-5; see infra. Surprisingly, these osteoinductive proteins exhibit a high affinity to metallic surfaces as demonstrated in the appended examples. An important precondition for such an adsorption process of to the metallic surface is a sufficient solubility of the proteins in the coating solution.

The device or implant of the invention, preferably, is any type of metallic surface as described above. Before contacting the solution comprising dissolved osteoinductive protein with a carrier containing a surface of metal or a metal alloy as described herein, it is envisaged that the respective metallic surface is preferably cleaned or treated to remove any surface contaminants and to promote good adhesion strength of the coating. Several methods which are suitable for this purpose are well-known in the art and also exemplified in the appended examples. For example, the metallic surface of the devices of the invention may be rinsed with e.g. acetone, alkyl alcohols like ethanol and then thoroughly rinsed with sterile distilled or demineralized water.

The device of the present invention, preferably, has an enlarged surface due to porous, beaded or meshed surface modifications. Such modifications can be introduced by methods well known in the art, including chemical or mechanical means. Moreover, it has been shown that the increased surface having irregularities in the nanometer and micrometer range are beneficial for osseointegration.

Many methods are described for the stabilization of proteins in pharmaceutical products. However, the experiments underlying this invention demonstrated that the well known techniques of protein stabilisation in liquid or freeze dried protein formulations can not be directly adapted to the adsorbed protein onto a metal surface. The coating of proteins onto metal surfaces e.g. titanium or titanium alloys according to the methods disclosed in the state of the art referred to supra cause the occurrence of modified species of the protein which result in aggregation or oxidation of the proteins (for details see Example 5). Moreover, even the addition of reducing agents does not decrease the amount of oxidized protein (for details see Example 10). Thanks to the method of the present invention it is possible to manufacture devices which after implantation will efficiently augment bone. Advantageously, the undesirable side effects, such as inflammation due to the enhanced immunogenicity of oxidized proteins, can be avoided. Moreover, the method of the present invention will allow a less time consuming and more cost effective manufacturing process for the medical devices of the present invention because coating of the metal or alloy corpus of the implant with a calcium phosphate or collagen layer is not required. Another advantage in this context is that potentially contaminated materials, such as collagens which may transmit infectious viruses, are excluded from the manufacturing process.

In a preferred embodiment of the method of this invention, steps (b) to (d) are carried out under an oxygen concentration of less than 10 vol % oxygen, preferably less than 5% and most preferably less than 2%.

In a further preferred embodiment of the method of this invention, steps (b) to (d) are carried out at a temperature below 25° C., preferably below 15° C. and most preferably below 8° C.

In a furthermore preferred embodiment of the method of this invention, said metal or metal alloy is titan or a titan alloy.

It is preferred that the metals/metal alloys of the invention are biocompatible. The term "biocompatible" means the quality of not having toxic or injurious effects on biological systems (Williams, D. F. 1999). Said properties are known for titan or titan alloys inter alia comprising those explicitly referred to infra.

More preferably, the titanium alloy is a titanium alloy containing at least 50% titanium. Furthermore preferably, said titan alloy is a Ti—Al—V-alloy, a Ti—Al—Fe alloy, a Ti—Al—Nb-alloy or a Ti—Mo—Zr—Al-alloy, most preferably Ti6A14V.

In a furthermore preferred embodiment of the method of this invention, the coating is carried out by dipping the metallic surface into said protein solution.

In another furthermore preferred embodiment of the method of this invention, the coating is carried out by dropping said protein solution onto the metallic surface.

Also encompassed as a preferred embodiment is a method, wherein the coating is carried out by spraying said protein solution onto the metallic surface.

The term "drying" encompasses means for removing liquids, such as excess buffer solution, which are still present after coating of the carrier with the osteoinductive protein. Preferably, drying is achieved by vacuum- or freeze-drying.

In another preferred embodiment of the method of this invention, the drying is achieved by evaporation at room temperature in an inert gas stream.

In a further preferred embodiment of the method of the invention said osteoinductive protein is a member of the TGF-β family.

The term "member of the TGF-β family" encompasses the biologically active, mature species of said proteins as well as the respective proforms, i.e. proproteins including the respective prodomain of these members of the TGF-β family as described in more detail below.

The TGF-β family of growth and differentiation factors has been shown to be involved in numerous biological processes comprising bone formation. All members of said family are secreted polypeptides comprising a characteristic domain structure. On the very N-terminus, the TGF-β family members comprise a signal peptide or secretion leader. This sequence is followed at the C-terminus by the prodomain and by the sequence of the mature polypeptide. The sequence of the mature polypeptide comprises seven conserved cysteines, six of which are required for the formation of intramolecular disulfide bonds whereas one is required for dimerization of two polypeptides. The biologically active TGF-β family member is a dimer, preferably composed of two mature polypeptides. The TGF-β family members are usually secreted as preproproteins comprising in addition to the mature sequence the pre (signalsequence)- and prosequence. The signalsequence and prodomains are extracellularly cleaved off and are not part of the signaling molecule. It has been reported, however, that the prodomain(s) may be required for extracellular stabilization of the mature polypeptides. An overview of the members of the TGF-β superfamily is given in: Wozney J M, Rosen V (1998): Bone morphogenetic protein and bone morphogenetic protein gene family in bone formation and repair. Clin Orthop 346: 26-37. The amino acid sequences of the members of the TGF-β family can be obtained from the well known databases such as Swiss-Prot via the internet (http://www.expasy.ch/sprot/sprot-top.html). Amino acid sequences for the preproforms of BMP2, BMP7 and GDF-5, members of the TGF-β family with a particularly high osteogenic potential, are also shown in SEQ ID No:1 to 3, respectively.

In the context of the present invention, the term "TGF-β family member" or the proteins of said family referred to below encompass all biologically active variants of the said proteins or members and all variants as well as their inactive precursors. Thus, proteins comprising merely the mature sequence as well as proteins comprising the mature protein and the prodomain or the mature protein, the prodomain and the leader sequence are within the scope of the invention as well as biologically active fragments thereof. Whether a fragment of a TGF-β member has the biological activity can be easily determined by biological assays described, e.g. in: Katagiri T, Yamaguchi A, Ikeda T, Yoshiki S, Wozney J M, Rosen V, Wang E A, Tanka H, Omura S, Suda T, (1990): The non-osteogenic mouse pluripotent cell line, C3H10T1/2, is induced to differentiate into osteoblastic cells by recombinant human bone morphogenetic protein-2. Biochem. Biophys. Res. Commun. 172: 295-299 or Nishitoh H, Ichijo H, Kimura M, Matsumoto T, Makishima F, Yamaguchi A, Yamashita H, Enomoto S, Miyazono K (1996): Identification of type I and type II serine/threonine kinase receptors for growth/differentiation factor-5. J. Biol. Chem. 271: 21345-21352.

Preferably, the biological activity according to the invention can be determined by in vivo models as described in the accompanied Examples. Furthermore, encompassed by the present invention are variants of the TGF-β members which have an amino acid sequences being at least 75%, at least 80%, at least 90%, at least 95%, at least 96%, at least 97%, at least 98% or at least 99% identical to the amino acid sequences of the members of the TGF-β family referred to herein, in particular to those shown in any one of SEQ ID Nos. 1 to 3.

More preferably, said member of the TGF-β family is a member of the BMP subfamily.

The members of the Bone Morphogenetic Protein (BMP) subfamily have been shown to be involved, inter alia, in the induction and re-modeling of bone tissue. BMPs were originally isolated from bone matrix. These proteins are characterized by their ability to induce new bone formation at ectopic sites. Various in vivo studies demonstrated the promotion of osteogenesis and chondrogenesis of precursor cells by BMPs and raise the possibility that each BMP molecule has distinct role during the skeletal development. More details about the molecular and biological properties of the BMPs are described in:

Wozney J M, Rosen V (1998): Bone morphogenetic protein and bone morphogenetic protein gene family in bone formation and repair. Clin Orthop 346: 26-27, Schmitt J, Hwang K, Winn, SR, Hollinger J (1999): Bone morphogenetic proteins: an update on basic biology and clinical relevance. J Orthop Res 17: 269-278 and Lind M (1996): Growth factors: possible new clinical tools. A review. Acta Orthop Scand 67: 407-17. Most preferably, said member of the BMP family is BMP2 or BMP7. The amino acid sequence for the preproform of BMP2 is deposited under Swiss-Prot Accession number P12643 and is shown below. Amino acids 1 to 23 correspond to the signal sequence, amino acids 24 to 282 correspond to the propeptide and amino acids 283 to 396 correspond to the mature protein. The amino acid sequence for the preproform of BMP7 is deposited under Swiss-Prot Accession number P18075 or shown in SEQ ID No: 2. Amino acids 1 to 29 correspond to the leader sequence, amino acids 30 to 292 correspond to the proform and amino acids 293 to 431 correspond to the mature protein. Preferably, BMP-2 or BMP7 refers to the preproform, to the proform or to the mature BMP-2 or BMP-7 peptide, respectively. Moreover also encompassed are fragments of said proteins having essentially the same biological activity, preferably osteoinductive properties. More sequence information for BMP2 and BMP7 is provided below. The amino acid sequence of the proform of BMP2 designated as proBMP-2 can, inter alia, be retrieved from Swiss-Prot under accession number Pro BMP2_HUMAN; P12643 and is also shown in SEQ ID NO: 4. In SEQ ID NO: 5 the amino acid sequence of rhproBMP-2 including an additional His-tag at the N-terminus is shown. rhproBMP2 is the recombinant form of human pro-BMP-2.

Both rhproBMP-2 shown in SEQ ID NO: 4 and rhproBMP-2 including an N-terminal His-tag shown in SEQ ID NO: 5 may, inter alia, be used in the appended Examples. However, the Examples are not limited to SEQ ID NO: 4 or 5, respectively. It is envisaged that the Examples herein below may also be carried out with any other amino sequence disclosed herein.

Also more preferably, said member of the TGF-β family is a member of the GDF subfamily.

Growth and Differentiation Factor (GDF) have been also shown to be involved, inter alia, in the induction and re-modeling of bone tissue. Growth Differentiation Factor 5 (GDF-5), also known as cartilage-derived morphogenetic protein 1 (CDMP-1) is a member of subgroup of the BMP family, which also includes other related proteins, preferably, GDF-6 and GDF-7. The mature form of the protein is a 27 kDa homodimer. Various in vivo and in vitro studies demonstrate the role of GDF-5 during the formation of different morphological features in the mammalian skeleton. Mutations of GDF-5 are responsible for skeletal abnormalities including decrease of the length of long bones of limbs, abnormal joint development in the limb and sternum (Storm & Kingsley (1999), Development Biology, 209, 11-27). The amino acid sequence between mouse and human is highly conserved.

Preferably, said member of the GDF subfamily is GDF-5. In a most preferred embodiment, said GDF-5 is recombinant human GDF-5 (rhGDF-5) as described in more detail below.

The amino acid sequence for the preproform of GDF-5 is deposited under Swiss-Prot Accession number P 43 0 26 or shown in SEQ ID No: 3. Amino acids 1 to 27 correspond to the leader sequence, amino acids 28 to 381 correspond to the proform and amino acids 382 to 501 correspond to the mature protein. Preferably, GDF-5 refers to the preproform, to the proform or to the mature GDF-5 peptide. Moreover also encompassed are fragments of GDF-5 having essentially the same biological activity, preferably osteoinductive properties. In a more preferred embodiment, said fragment comprises amino acids 383 to 501 of the sequence shown in SEQ ID No: 3. It is also envisaged that any combination of the above-mentioned members of the TGF-β family can be used in the solution which is employed in the method of the invention. The following tables show amino acid sequences for the preproforms of BMP-2, BMP-7 and GDF-5:

Preproform of human BMP-2 (Swiss-Prot Prim. Accession Number P12643);
SEQ ID No. 1:

| Key | From | To | Length |
|---|---|---|---|
| SIGNAL | 1 | 23 | 23 |
| PROPEP | 24 | 282 | 259 |
| hBMP2 | 283 | 396 | 114 |

Preproform of human BMP-2 (Swiss-Prot Prim. Accession Number P12643);
SEQ ID No. 1:

```
         10         20         30         40         50         60
          |          |          |          |          |          |
MVAGTRCLLA LLLPQVLLGG AAGLVPELGR RKFAAASSGR PSSQPSDEVL SEFELRLLSM 70         80         90        100        110        120
          |          |          |          |          |          |
FGLKQRPTPS RDAVVPPYML DLYRRHSGQP GSPAPDHRLE RAASRANTVR SFHHEESLEE 130        140        150        160        170        180
          |          |          |          |          |          |
LPETSGKTTR RFFFNLSSIP TEEFITSAEL QVFREQMQDA LGNNSSFHHR INIYEIIKPA 190        200        210        220        230        240
          |          |          |          |          |          |
TANSKFPVTR LLDTRLVNQN ASRWESFDVT PAVMRWTAQG HANHGFVVEV AHLEEKQGVS 250        260        270        280        290        300
          |          |          |          |          |          |
KRHVRISRSL HQDEHSWSQI RPLLVTFGHD GKGHPLHKRE KRQAKHKQRK RLKSSCKRHP 310        320        330        340        350        360
          |          |          |          |          |          |
LYVDFSDVGW NDWIVAPPGY HAFYCHGECP FPLADHLNST NHAIVQTLVN SVNSKIPKAC 370        380        390
          |          |          |
CVPTELSAIS MLYLDENEKV VLKNYQDMVV EGCGCR
```

References

[1] SEQUENCE FROM NUCLEIC ACID. MEDLINE = 89072730; PubMed = 3201241; Wozney J. M., Rosen V., Celeste A. J., Mitsock L. M., Whitters M. J., Kriz R. W., Hewick R. M., Wang E. A.; "Novel regulators of bone formation: molecular clones and activities."; Science 242:1528-1534(1988).

[2] X-RAY CRYSTALLOGRAPHY (2.7 ANGSTROMS) OF 292-396. MEDLINE = 99175323; PubMed = 10074410; Scheufler C., Sebald W., Huelsmeyer M.; "Crystal structure of human bone morphogenetic protein-2 at 2.7 A resolution."; J. Mol. Biol. 287:103-115(1999).

Preproform of human BMP-7 (Swiss-Prot Prim. Accession. Number: P18075);
SEQ ID No. 2:

| Key | From | To | Length |
|---|---|---|---|
| SIGNAL | 1 | 29 | 29 |
| PROPEP | 30 | 292 | 263 |
| hBMP-7 | 293 | 431 | 139 |

```
         10         20         30         40         50         60
          |          |          |          |          |          |
MHVRSLRAAA PHSFVALWAP LFLLRSALAD FSLDNEVHSS FIHRRLRSQE RREMQREILS
         70         80         90        100        110        120
          |          |          |          |          |          |
ILGLPHRPRP HLQGKHNSAP MFMLDLYNAM AVEEGGGPGG QGFSYPYKAV FSTQGPPLAS
        130        140        150        160        170        180
          |          |          |          |          |          |
LQDSHFLTDA DMVMSFVNLV EHDKEFFHPR YHHREFRFDL SKIPEGEAVT AAEFRIYKDY
        190        200        210        220        230        240
          |          |          |          |          |          |
IRERFDNETF RISVYQVLQE HLGRESDLFL LDSRTLWASE EGWLVFDITA TSNHWVVNPR 250        260        270        280        290        300
          |          |          |          |          |          |
HNLGLQLSVE TLDGQSINPK LAGLIGRHGP QNKQPFMVAF FKATEVHFRS IRSTGSKQRS
        310        320        330        340        350        360
          |          |          |          |          |          |
QNRSKTPKNQ EALRMANVAE NSSSDQRQAC KKHELYVSFR DLGWQDWIIA PEGYAAYYCE
        370        380        390        400        410        420
          |          |          |          |          |          |
GECAFPLNSY MNATNHAIVQ TLVHFINPET VPKPCCAPTQ LNAISVLYFD DSSNVILKKY
        430
          |
RNMVVRACGC H
```

References

[1] SEQUENCE FROM NUCLEIC ACID, AND PARTIAL SEQUENCE. TISSUE = Placenta; MEDLINE = 90291971; PubMed = 2357959; Oezkaynak E., Rueger D. C., Drier E. A., Corbett C., Ridge R. J., Sampath T. K., Oppermann H.; "OP-1 cDNA encodes an osteogenic protein in the TGF-beta family."; EMBO J. 9:2085-2093(1990).

-continued

Preproform of human BMP-7(Swiss-Prot Prim. Accession. Number: P18075);
SEQ ID No. 2:

[2] SEQUENCE FROM NUCLEIC ACID. MEDLINE = 91088608; PubMed = 2263636; Celeste A. J., Iannazzi J. A., Taylor R. C., Hewick R. M., Rosen V., Wang E. A., Wozney J. M.; "Identification of transforming growth factor beta family members present in bone-inductive protein purified from bovine bone."; Proc. Natl. Acad. Sci. U.S.A. 87:9843-9847(1990).
[3] X-RAY CRYSTALLOGRAPHY (2.8 ANGSTROMS) OF 293-431. MEDLINE = 96149402; PubMed = 8570652; Griffith D. L., Keck P. C., Sampath T. K., Rueger D. C., Carlson W. D.; "Three-dimensional structure of recombinant human osteogenic protein 1: structural paradigm for the transforming growth factor beta superfamily."; Proc. Natl. Acad. Sci. U.S.A. 93:878-883(1996).

Preproform of human GDF-5 (Swiss-Prot Prim. Accession Number: P 43026);
SEQ ID No. 3:

| Key | From | To | Length |
|---|---|---|---|
| SIGNAL | 1 | 27 | 27 |
| PROPEP | 28 | 381 | 354 |
| hGDF-5 | 382 | 501 | 120 |

```
            10         20         30         40         50         60
             |          |          |          |          |          |
        MRLPKLLTFL LWYLAWLDLE FICTVLGAPD LGQRPQGSRP GLAKAEAKER PPLARNVFRP 70         80         90        100        110        120
             |          |          |          |          |          |
        GGHSYGGGAT NANARAKGGT GQTGGLTQPK KDEPKKLPPR PGGPEPKPGH PPQTRQATAR 130        140        150        160        170        180
             |          |          |          |          |          |
        TVTPKGQLPG GKAPPKAGSV PSSFLLKKAR EPGPPREPKE PFRPPPITPH EYMLSLYRTL 190        200        210        220        230        240
             |          |          |          |          |          |
        SDADRKGGNS SVKLEAGLAN TITSFIDKGQ DDRGPVVRKQ RYVFDISALE KDGLLGAELR 250        260        270        280        290        300
             |          |          |          |          |          |
        ILRKKPSDTA KPAVPRSRRA AQLKLSSCPS GRQPAALLDV RSVPGLDGSG WEVFDIWKLF
           310        320        330        340        350        360
             |          |          |          |          |          |
        RNFKNSAQLC LELEAWERGR TVDLRGLGFD RAARQVHEKA LFLVFGRTKK RDLFFNEIKA
           370        380        390        400        410        420
             |          |          |          |          |          |
        RSGQDDKTVY EYLFSQRRKR RAPLATRQGK RPSKNLKARC SRKALHVNFK DMGWDDWIIA
           430        440        450        460        470        480
             |          |          |          |          |          |
        PLEYEAFHCE GLCEFPLRSH LEPTNHAVIQ TLMNSMDPES TPPTCCVPTR LSPISILFID
           490        500
             |          |
        SANNVVYKQY EDMVVESCGC R
```

References
[1] SEQUENCE FROM NUCLEIC ACID. TISSUE = Placenta; MEDLINE = 95071375; PubMed = 7980526; Hoetten G., Neidhardt H., Jacobowsky B., Pohl J.; "Cloning and expression of recombinant human growth/differentiation factor 5."; Biochem. Biophys. Res. Commun. 204:646-652(1994).
[2] SEQUENCE FROM NUCLEIC ACID. TISSUE = Articular cartilage; MEDLINE = 95050604; PubMed = 7961761; Chang S., Hoang B., Thomas J. T., Vukicevic S., Luyten F. P., Ryba N. J. P., Kozak C. A., Reddi A. H., Moos M.; "Cartilage-derived morphogenetic proteins. New members of the transforming growth factor-beta superfamily predominantly expressed in long bones during human embryonic development."; J. Biol. Chem. 269:28227-28234(1994).

It may be that the above-shown published sequences when retrieved from Swiss-Prot contained (an) error(s), for example, caused by inaccuracies during sequencing. As a consequence such sequencing errors may lead to (a) silent mutation(s) or to alteration of (a) codon(s) which, thus, encode(s) (an) other amino acid(s) as previously published. However, since Swiss-Prot is updated in an event sequencing errors are assumed to have been occurred, the most recent sequence(s) may be retrieved from Swiss-Prot under the reference number or under the respective name of the polypeptides indicated supra.

For example, SEQ ID NO: 3 may comprise the following amino acid replacements in the proform of the preproform of human GDF-5: at position 38 the amino acid serine (S) is replaced by the amino acid threonine (T), at position 254 of SEQ IS NO: 3 the amino acid valine (V) is replaced by the amino acid alanine (A), at position 256 of SEQ IS NO: 3 the amino acid arginine (R) is replaced by the amino acid glycine (G), at position 257 of SEQ IS NO: 3 the amino acid serine (S) is replaced by the amino acid glycine (G), at position 258 of SEQ IS NO: 3 the amino acid arginine (R) is replaced by the amino acid glycine (G), at position 276 the amino acid alanine (A) is replaced by the amino acid serine (S) and at position 321 of SEQ IS NO: 3 the amino acid threonine (T) is replaced by the amino acid alanine (A). The resulting amino acid sequence in which the before-mentioned amino acid replacements may occur is shown in SEQ ID NO: 6. It is to be understood that (an) amino acid replacement(s) in the proform of the amino acid sequence of the preproform of GDF-5 shown in SEQ ID NO: 3 does/do not alter, change or abolish the physiological function(s) of GDF-5. In the context of the present application, it is envisaged that SEQ ID NO: 6 may be also used in connection with the means and methods of the present invention.

In a further preferred embodiment of the method of the invention said device is free of toxic substances.

The term "toxic substances", preferably, encompasses those toxic organic solvents and additives which are used by the methods described in the art, e.g. acetonitrile or chromosulfuric acid. Said substances may cause inflammation and other reactions after implantation of devices containing said substances. Said devices are therapeutically less acceptable due to said undesirable side effects which can not be avoided by the coating methods and some of the surface treatment methods as described in the art. Moreover, the international guidance for the development of therapeutic proteins require that in the manufacturing process harmful and toxic substances should be avoided (for details see: International Conference on Harmonisation (ICH), Topic Q3C; www.emea.e-u.int/). However, the device of the present invention or a device which is obtainable by the method of the present invention is, advantageously, free of said toxic substances and, therefore, therapeutically well acceptable and fulfills the requirements of the regulatory authorities.

In a further preferred embodiment of the method of the invention, said solution allows the dissolution of said protein for a time sufficient for homogenous coating of said metallic surface of the carrier.

The term "solution which allows the dissolution of said protein for a time sufficient for homogenous coating of said metallic surface of the carrier" refers to a solution in which the osteoinductive proteins can be efficiently dissolved. Homogenous coating means that the surface of the carrier is entirely coated with the said osteoinductive protein after treatment with the said solution. A homogenous coating is characterized in that essential identical amounts of protein are present in each and every area of the surface of said carrier. Homogenous coating is a prerequisite for efficient release and homogenous distribution and activity of the osteoinductive protein into the tissue surrounding the site of implantation. Moreover, it is to be understood that the osteoinductive proteins are not aggregated and partially or entirely inactivated due to precipitation or micro-precipitation, rather attachment of biologically active, non-aggregated proteins is to be achieved by homogenous coating. Said homogenous coating can be achieved by the method of the present invention and as described in the accompanied Examples. Further, means and methods for controlling homogeneous coating, quantification and characterization of the immobilized protein are described in the accompanied Examples. The solution can be composed by the person skilled in the art based on the solubility of the osteoinductive protein which depends on the pH, the ionic strength and the influence of the carrier on said parameters after contacting the carrier with said solution. In accordance with the present invention it has been found that a suitable solution for the method of the present invention comprises only components which do not influence the oxidation status of the osteoinductive protein. For example, saccharides like sucrose or trehalose (for details see example 9) which are often used as excipients in protein formulations (stabilizer and bulking agent) cannot be used for the coating process because they reduce the binding of the protein onto the metal surface. Further components which should be avoided are described in the accompanied Examples below.

In accordance with the method of the present invention said solution allows a concentration of said osteoinductive protein of more than 0.5 mg/ml, preferably of more than 2 mg/ml and most preferably more than 3 mg/ml.

Also preferred is a method in which said solution has an acidic pH.

The term "weak acid" refers to organic or inorganic compounds containing at least one ionogenically bound hydrogen atom. Weak acids are well known in the art and are described in standard text books, such as Römpp, lexicon of chemistry. Preferably, said weak acids which have low dissociation degrees and are described by pK values between 3 and 7, preferred between 4 and 6.

Most preferably, said acidic solution contains HCl, acetic acid, citric acid and/or succinic acid.

In another most preferred embodiment of the method of this invention, the concentration of the acid is less than or equal to 100 mmol/l, preferably less than 50 mmol/l and more preferably less than 25 mmol/l and most preferably less than 15 mmol/l.

In another most preferred embodiment of the method of this invention, the solution is saturated with an inert gas, most preferably with nitrogen, argon or helium. In its most preferred embodiment, the method of this invention is carried out in a compartment with a controlled atmosphere, humidity, temperature and a defined atmosphere exchange rate.

The present invention further relates to a device which is obtainable by the method of the present invention.

The definitions and explanations of the terms made before in context with the methods of the present invention apply mutates mutandis for the devices described infra.

Said device is characterized by the features which are contributed by the aforementioned methods. In particular, the device comprises an osteoinductive protein which is homogenously coated on a metal or alloy porous or non-porous surface of the device, whereby the oxidation status of the osteoinductive protein is not significantly enhanced in comparison to osteoinductive protein which has not been coated onto the said metal or alloy surface. Preferred devices are described in the accompanied Examples in detail.

The invention encompasses a pharmaceutical composition comprising the device of the invention or a device which is obtainable by the method of the invention.

The definitions and explanations of the terms made before in context with the methods and devices of the present invention apply mutatis mutandis for the pharmaceutical compositions described herein.

The invention also encompasses the use of the device of the invention or a device which is obtainable by the method of the invention for the preparation of a pharmaceutical composition to be used for an accelerated osseointegration and new bone formation. The definitions of the terms referred to above apply mutatis mutandis to the aforementioned use of the present invention and those described infra.

The term "osseointegration and new bone formation" describes that bone has the ability to form new bone around the implant and to integrate with the implant. Integration means the attachment of bone cells to the implant surface resulting in a firm and permanent anchorage of the prosthetic reconstruction under functional load without pain, inflammation or loosening.

More preferably, said accelerated osseointegration and new bone formation is to be carried out for treatment of traumatic, malignant or artificial defects, for the treatment of dental defects or for the treatment of hip, elbow, spine, knee, finger or ankle joint. The symptoms of the diseases and disorders referred to hereinabove are described in detail in standard text books of medicine, such as Pschyrembel and Stedman.

Also within the scope of the present invention is a method for treating one or more of the diseases referred to in accordance with the uses of the present invention, wherein said method comprises at least the step of administering the device of the invention or a device which can be obtained by the method of the invention in a pharmaceutically acceptable form to a subject. Preferably, said subject is a human.

Finally, the invention relates to a kit comprising the device of the invention or a device which is obtainable by the method of the invention.

The definitions and explanations of the terms made before in context with the methods, devices, pharmaceutical compositions and uses of the present invention apply mutatis mutandis for the kit described herein.

The parts of the kit of the invention can be packaged individually in vials or other appropriate means depending on the respective ingredient or in combination in suitable containers or multicontainer units. Manufacture of the kit follows preferably standard procedures which are known to the person skilled in the art. Preferably, the device is packaged in a container or vial in a oxygen free atmosphere, such as an inert gas atmosphere, preferably consisting of nitrogen.

The figures show:

FIG. 1: Percentage of oxidized rhGDF-5 after extraction with 10 mmol/l HCl.

Figure 2:
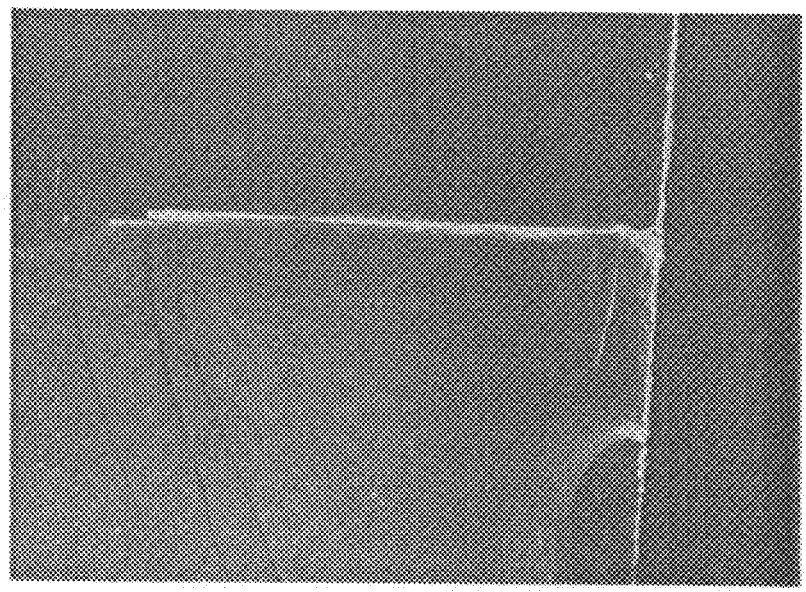

FIG. 2: Fluorescence staining of a metal sheet coated with rhGDF-5 in 10 mM HCl.

Figure 3:
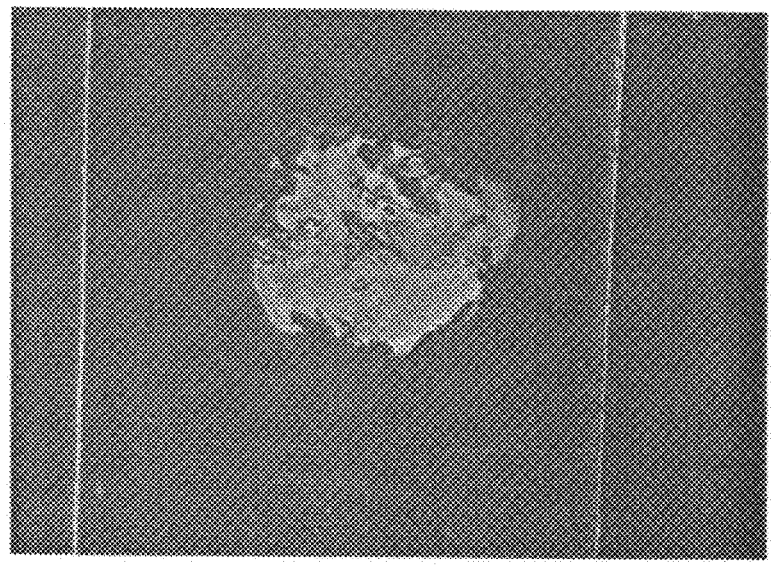

FIG. 3: Fluorescence staining of a metal sheet coated with rhGDF-5 in PBS.

Figure 4:
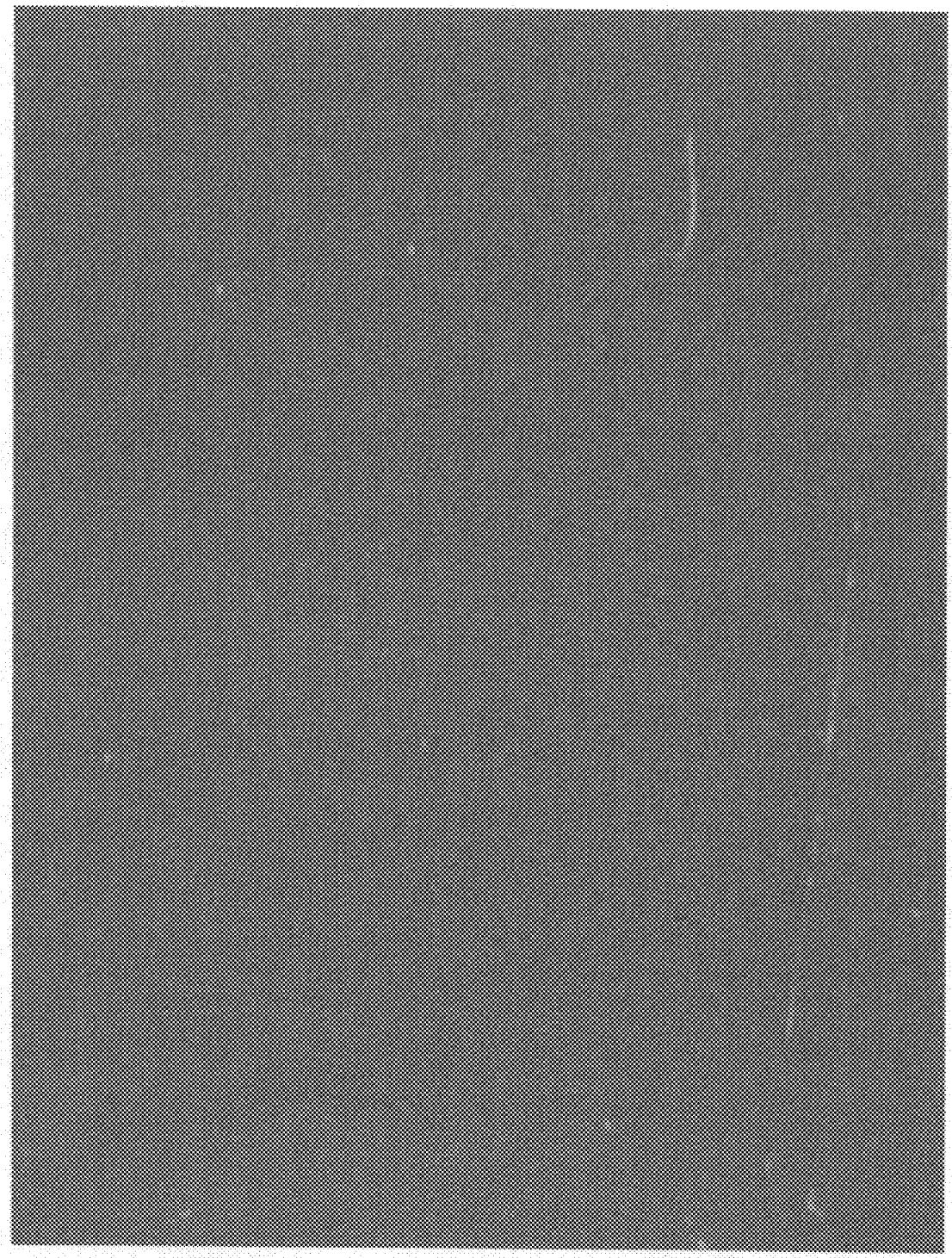

FIG. 4: Fluorescence staining of a metal sheet coated with 10 mmol/l HCl.

Figure 5:
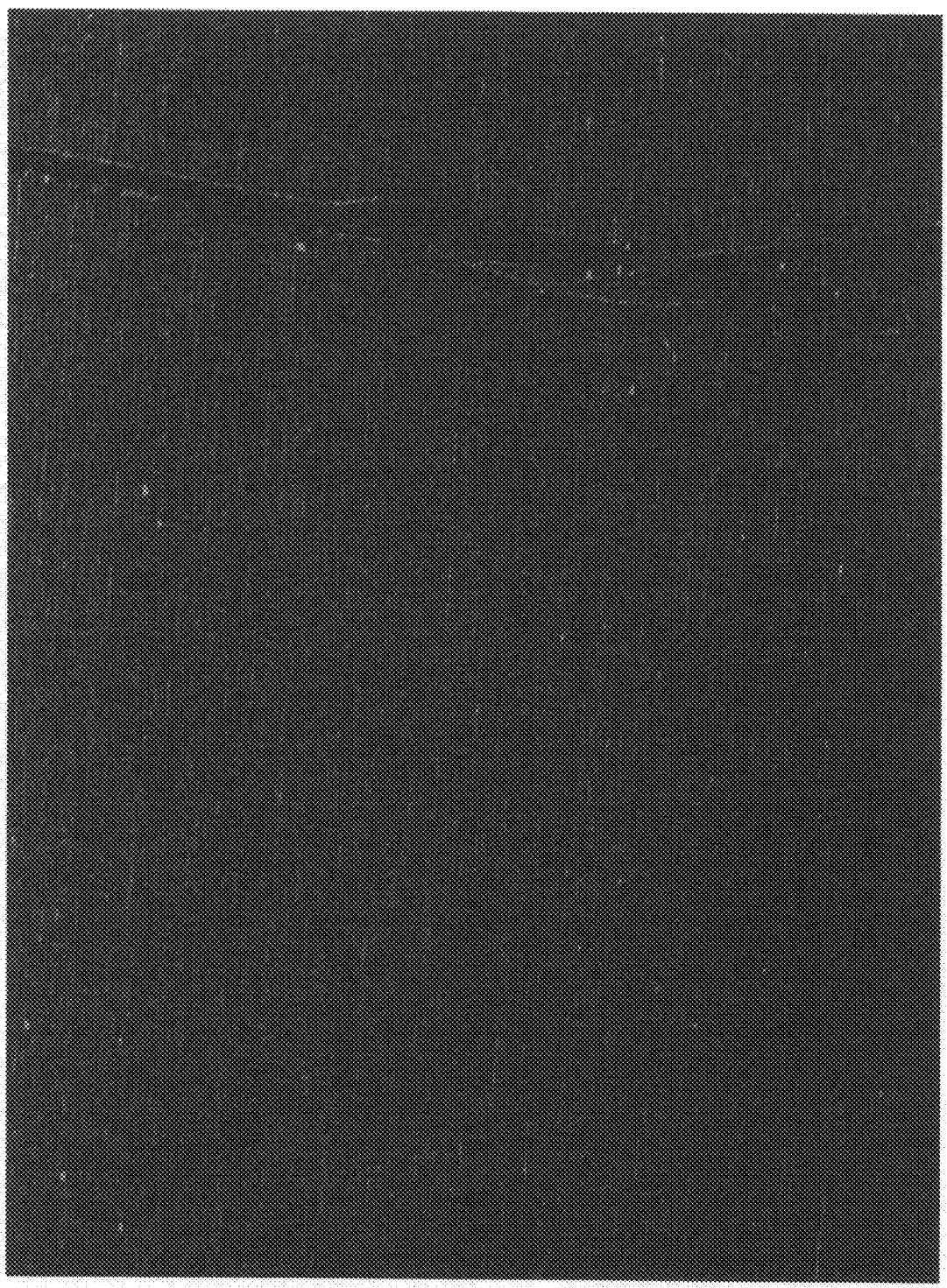

FIG. 5: Fluorescence staining of a blank metal sheet.

Figure 6:
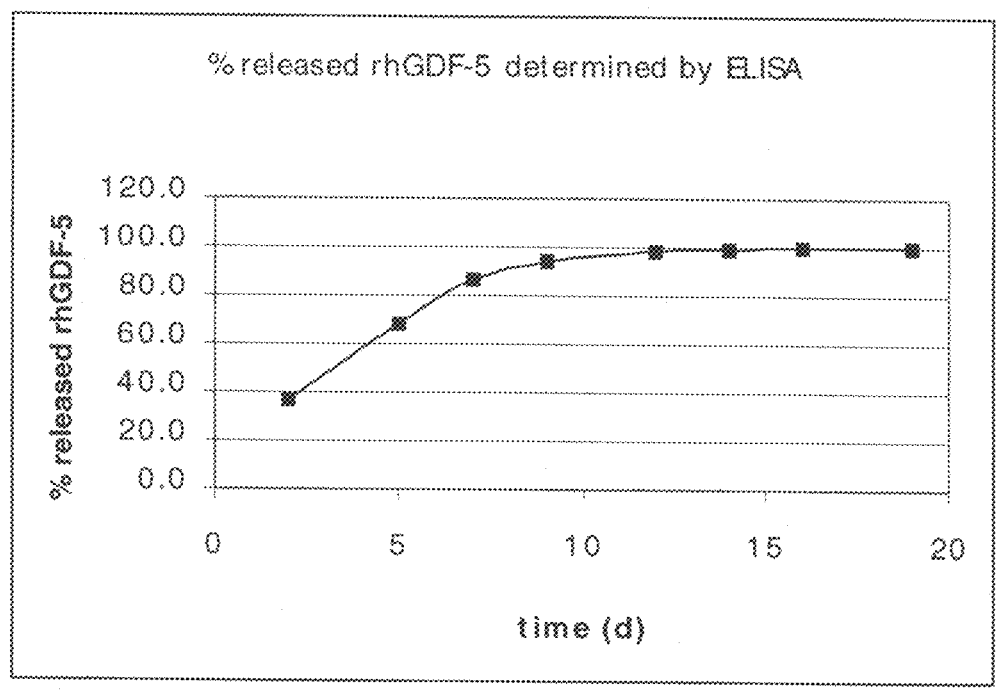

FIG. 6: Release of rhGDF-5 from pretreated titanium surfaces. Summary of the results as determined by ELISA.

Figure 7:
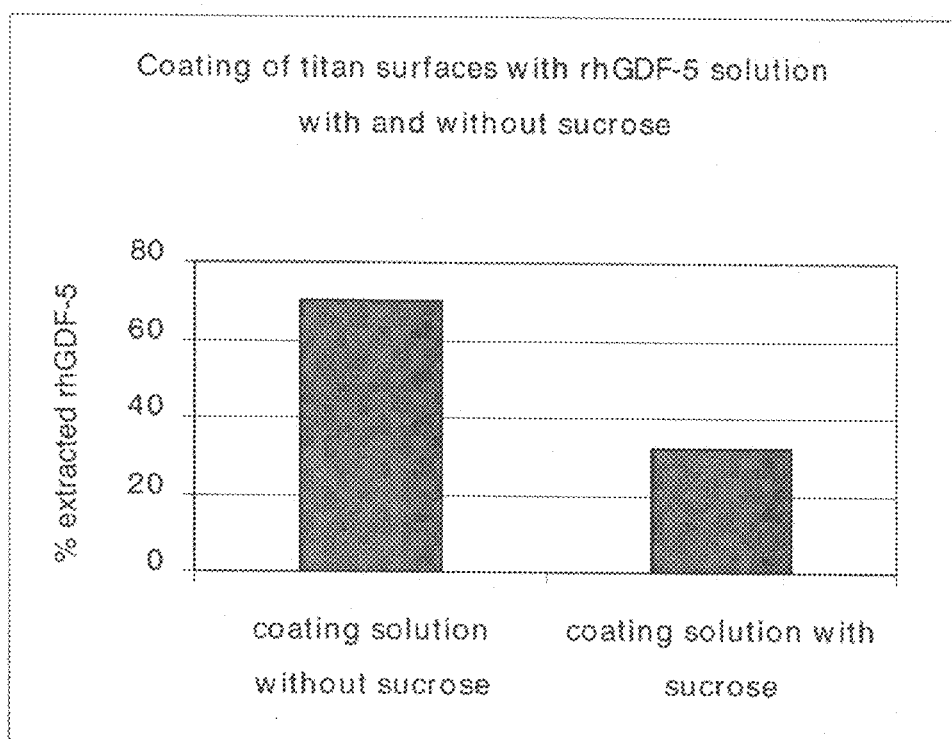

FIG. 7: Coating of titanium surfaces with rhGDF-5 solution with and without sucrose.

Figure 8:
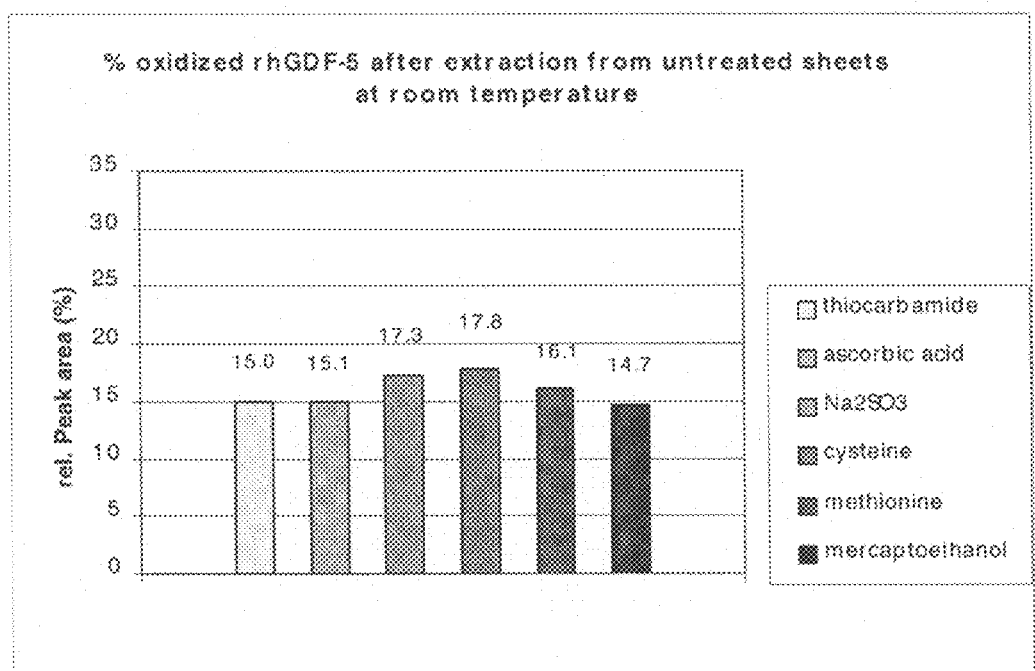

FIG. 8: Percentage of oxidized rhGDF-5 after extraction from pretreated sheets at room temperature.

Figure 9:
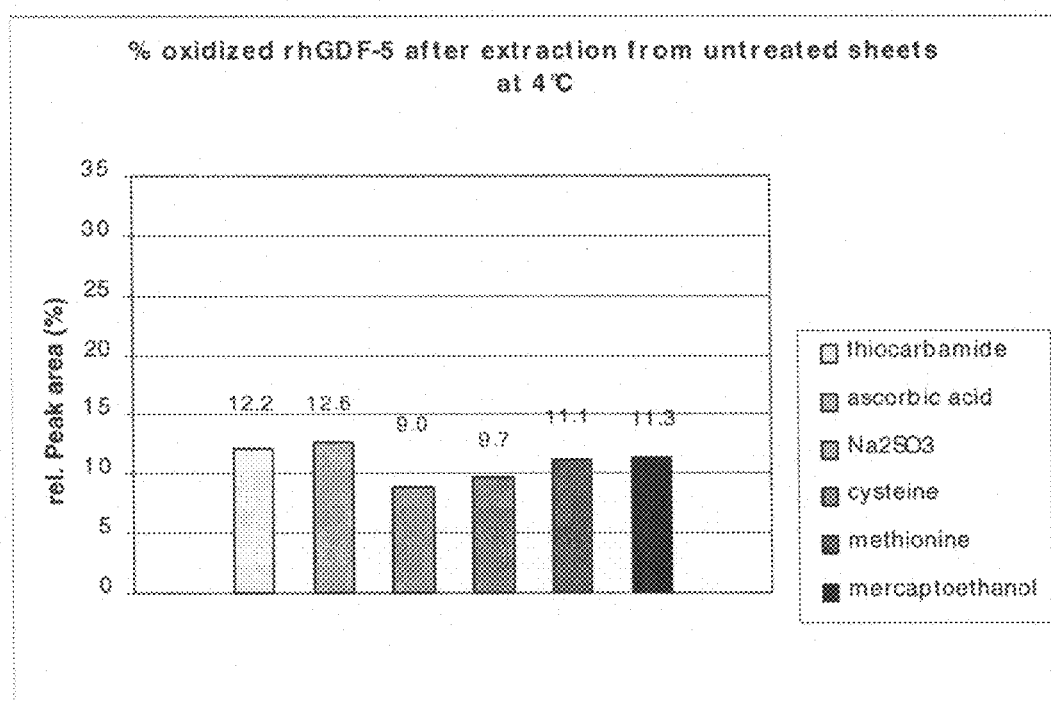

FIG. 9: Percentage of oxidized rhGDF-5 after extraction from pretreated sheets at 4° C.

Figure 10:
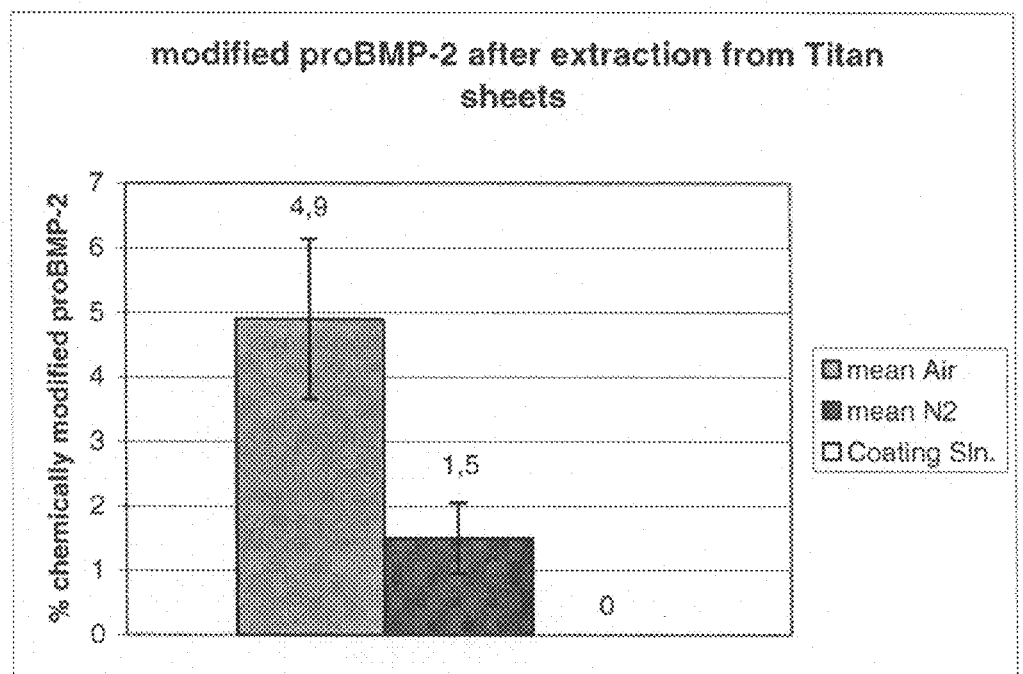

FIG. 10: Increase of modified rhproBMP-2 after coating/extraction compared to the coating solution The invention will now be described by reference to the following biological examples which are merely illustrative and are not construed as a limitation of the scope the present invention.

EXAMPLE 1

Quantification of rhGDF-5 by Means of RP-HPLC

The amount of rhGDF-5 is determined by reversed phase HPLC analysis. The sample is applied to a Poros C8-18-column (R2/10, 21.×30 mm) which has been equilibrated with 0.1% formic acid, 21% acetonitrile. After washing of the column, the elution takes place with 0.1% formic acid, and a gradient of 21-84% acetonitrile (flow: 0.4 ml/min). The elution is observed by measuring the absorbance at 220 nm. The quantification takes place via the peak and use of a standard curve just taken.

EXAMPLE 2

Extraction and Quantification of the Bound Protein

The protein was extracted by incubation of the coated body first in PBS for 1 h at room temperature. Subsequently the coated body was incubated in 10 mmol/l HCl for 3 h at room temperature. After adjusting the PBS sample to pH 2, the PBS and HCl solutions containing extracted bone growth factor were analysed by RP-HPLC as described in example 1.

EXAMPLE 3

Quantification of Soluble Aggregates in Solutions Containing Extracted Protein

The amount of soluble aggregates in samples containing extracted protein was determined by size exclusion HPLC. The column (TSK 3000) was equilibrated with 50 mmol/l acetic acid, 50 mmol/l phosphoric acid, NaOH, pH 3.0.

The elution is observed by UV-detection at 220 nm. The quantification takes place via the ratio aggregate peak area in relation to the total peak area.

EXAMPLE 4

Determination of Chemical Modifications of the Extracted Protein

The amount of chemical modifications i.e. oxidation of bone growth factor in solutions containing extracted protein was determined by RP-HPLC. The sample is applied to a Vydak C8-18 column (2×250 mm) which has been equilibrated with 0.15% TFA, 20% acetonitrile. After washing of the column, the elution of the bone growth factor takes place with 0.1% TFA, and a stepwise gradient of 20%-84% acetonitrile (flow: 0.3 ml/min). The elution is observed by measuring the absorbance at 220 nm. The quantification takes place via the ratio peak area of modified species in relation to the total peak area.

EXAMPLE 5

Coating and Release of Ti6Al4V with Bone Growth Factor rhGDF-5 may be oxidized to a significant extent after the coating—release cycle using titanium sheets as surface. Here we describe a method and a device for coating avoiding protein oxidation during the coating procedure.

Device for coating titanium or titanium alloy with bone growth factor:

The coating process is performed under an inert gas atmosphere to exclude oxygen. To maintain these conditions a chamber is used. The chamber consists of a hermetically closed room with a continuous stream of inert gas, e.g. $N_2$ gas. Inside the chamber a slight excess pressure is maintained. The materials needed for the coating process are transported into the chamber through a gas tight lock. The chamber allows a manually as well as an automated coating process. For the definition and standardization of the coating process the relative humidity in the chamber is monitored and adjusted.

Coating:

The titan sheets were cleaned, washed with demineralized water and dried. The titanium sheets were coated with 60μg of rhGDF-5. Each sheet was laid down flat in a dish and coated with rhGDF-5 solution on one side of the metal sheet. Coating was performed under $N_2$ gas atmosphere in a chamber as described above and at a temperature of 0° C. to 4° C. After coating the sheet was dried at the respective conditions for 30 min under vacuum.

Extraction:

rhGDF-5 was incubated first in PBS to mimic near physiological conditions. To keep samples nearly free of oxygen, the PBS solution was saturated with $N_2$ gas for the respective samples.

After PBS incubation the sheets were incubated in 10 mmol/l HCl for 3 h at the respective temperature. The rhGDF-5 in the extraction solutions was quantified by RP-HPLC (see example 1). The amount of oxidized rh-GDF-5 was also determined by RP-HPLC (see example 4).

To be able to compare samples coated and extracted as described above, the same procedure was performed at room temperature and under oxygen atmosphere.

TABLE 1

| Sample | Atmosphere | Temperature | % oxidized protein after extraction (Mean) | SD |
|---|---|---|---|---|
| Implant | air | RT | 10.0 | 1.6 |
| Implant | $N_2$ | 4° C. | 5.6 | 0.6 |
| Bulk | air | RT | 4.7 | 0.0 |

The parameters tested in the experiments here have an influence on the amount of oxidized rhGDF-5 after extraction from the titanium sheets: Samples coated in the presence of air oxygen at room temperature reveal an amount of oxidized rhGDF-5 of 10.0%±1.6% as displayed in table 1 and FIG. 1.

The samples processed at 4° C. and under $N_2$ gas show 5.6%±0.6% oxidized rhGDF-5 after extraction. Compared to rhGDF-5 bulk solution the samples processed at 4° C. and $N_2$ gas reveal no significant difference in the amount of oxidized rhGDF-5 (4.7%±0%).

EXAMPLE 6

Determination of the Homogeneity of the Coating of Bone Growth Factor on Titanium Surfaces by Fluorescence Microscopy We investigated the coating density of bone growth factor on the titan body by using a fluorescence marker for proteins. The determination was performed by fluorescence microscopy.

Coating:

One sheet was laid down flat in a dish and coated with 10 μl of a 6.18 mg/ml 10 mmol/l HCl rhGDF-5 solution on one side of the metal sheet. A second sheet was coated with 10 μl of a 10 mmol/l HCl. The sheets were dried for 30 min under vacuum. A third sheet was not coated and used as blank. Additionally a sheet was coated with rhGDF-5 solution 6.0 mg/ml in PBS.

Fluorescence Dying of the Protein:

2.3 μl of a 10 mmol/l solution of Alexa Fluor™ 488 were added to 1 ml of a 0.15 M $NaHCO_3$ solution. The 3 metal sheets were incubated in 1 ml of the fluorescence dye mixture in the dark for 4 h at room temperature. The ratio protein: fluorophor is 1:10. The sheet used as blank was incubated for 20 min only. After the incubation period the sheets were extensively washed with demineralized water and dried for 15 min under vacuum in the dark.

The fluorescence signal was detected by fluorescence microscopy and documented by an imaging software.

In FIG. 2 the area coated with rhGDF-5 can be clearly determined by fluorescence microscopy. Meaning the fluorescence marker bound to the protein. In contrast FIG. 3 demonstrates the importance of the solvent of rhGDF-5 as a coating solution containing PBS leads to inhomogeneous distribution of the protein and protein dots.

To exclude artifacts in FIG. 4 the sheet coated with 10 mmol/l HCl is displayed. 10 mmol/l HCl is the solvent of rhGDF-5 in solution.

To exclude any effects of the solvent we also prepared a blank sheet that was not coated with rhGDF-5 or 10 mmol/l HCl but also incubated in fluorescence marker Alexa Fluor™ 488 (FIG. 5).

The pictures demonstrate clearly that only rhGDF-5 is dyed by the fluorescence marker. Furthermore the distribution of the protein on the surface is regular when the solvent used is 10 mmol/l HCl.

EXAMPLE 7

Long Term in Vitro Release of Bone Growth Factor from Pretreated Titanium Surfaces We developed a method for coating bone growth factor on titanium surfaces. After standardized extraction we are able to analyze the protein for aggregates (Example 3), the amount of oxidized bone growth factor (Example 4) and are able to quantify the extracted protein (Example 1). In the experiment described here we determined the release kinetics of bone growth factor by incubation of coated titanium sheets in cell culture medium for 30 days. To mimic physiological conditions and metabolic activity, we exchanged the medium every 48 h and quantified the amount of released protein by ELISA.

Coating:

The sample was coated as described in example 5.

30 Days Release:

The sheet was incubated in 6 ml of release medium: 89% αMEM, 1% penicillin, streptomycin, 10% FCS for 30 days at 4° C. The samples were permanently rolled in a mixer. After every 48 h of incubation the supernatant was taken and stored frozen at −70° C. A volume of 6 ml of fresh medium was added to the release samples. The released protein in the samples was quantified by bone growth factor ELISA. The wells of 96-well-plate are coated with a monoclonal antibody against rhGDF-5. After washing the plate with PBS containing 0.05% Tween 20 and blocking with SuperBloc solution (Pierce, cat-no. 37515) the rhGDF-5 containing samples are added and the plate is incubated for 60 min at room temperature. After washing the samples (see above) a second biotinylated antibody against rhGDF-5 is added and the samples are incubated for 60 min at room temperature. After washing step a strepavidin peroxidase complex is added and the samples are incubated for 60 min at room temperature. Subsequently, the wells are washed with PBS, containing 0.05% Tween 20 and the amount of bound peroxidase is quantified using BM Blue-POD-substrate (Roche Diagnostics, Cat-No.: 1 484 28). The detection wavelength is 450 nm, the reference wave length is 630 nm. The amount of rhGDF-5 is calculated using a rhGDF-5 standard curve.

The results of the bone growth factor release determined by ELISA are summarized in table 2 & FIG. 6. The amount of released protein after 30 days determined by ELISA is 100.4±0.8

TABLE 2

| Day | ELISA: % protein extracted |
|---|---|
| 2 | 37.1 |
| 5 | 68.7 |
| 7 | 87.0 |
| 9 | 94.0 |
| 12 | 98.0 |
| 14 | 99.1 |
| 16 | 99.7 |
| 19 | 100.4 |

EXAMPLE 8

Coating and Extraction of Titanium or Titanium Alloy with rhBMP-2

Here we investigated the behavior of rhBMP-2 during the coating-extraction process: rhBMP2 is like rhGDF-5 a further member of the TGF-β protein family.

Coating:

The sheets were laid down flat in a dish and coated with either 10 µl of a 6.0 mg/ml bone growth factor or rhBMP2 solution on one side of the sheet. All sheets were dried for 30 min under vacuum.

Extraction:

All sheets were extracted with PBS for 1 h at room temperature. Then the sheets coated with bone growth factor and rhBMP2 were incubated in 10 mmol/l HCl for 3 h. The results of the experiments described above are summarized in table 3.

TABLE 3

| Sample No | protein | % of protein extracted in PBS | % protein extracted in 10 mmol/l HCl | Total recovery of protein in % |
|---|---|---|---|---|
| 1 | rhGDF-5 | 8.8 | 83.2 | 92.0 |
| 2 | rhBMP2 | 0 | 111.3 | 111.3 |
| 3 | rhBMP2 | 0 | 105.1 | 105.1 |

There was no rhBMP-2 extracted during incubation in PBS. 8.8% of rhGDF-5 were extracted in PBS.

The results indicate that proteins originating from the TGFβ protein family bind to metal surfaces and can be (almost) completely extracted in 10 mmol/l HCL after incubation in PBS.

EXAMPLE 9

Coating of Titanium or Titanium an Alloy with Bone Growth Factor in the Presence of Sucrose Here we describe the coating of titanium surfaces with rhGDF-5 solution with 10% sucrose. In comparison we coated titan surfaces with bone growth factor in 10 mmol/lHCl.

The titan sheets were washed with demineralized water, dried and coated with 40 µg bone growth factor in 10 mmol/l HCl or 40 µg bone growth factor in 10% sucrose, 10 mmol/L HAc and 5 mmol/l HCl), respectively.

Subsequently the titanium material was washed in PBS for 1h at room temperature. Then the protein was extracted by incubation in 100 mmol/l HCl for 3 h at room temperature. The protein content of all solutions was determined by RP-HPLC quantification. Before quantification the PBS solution was adjusted to pH 2 to increase the solubility of bone growth factor.

In the experiments described herein, two different coated metal pieces were prepared: Titanium sheets coated with bone growth factor solutions with or without 10% sucrose. The results of the coating and extraction procedure are summarized in Table 4:

TABLE 4

| Sample No: | Without sucrose | With 10% sucrose |
|---|---|---|
| Mass of protein on titan body after coating (µg) | 4.5 | 4.5 |
| Bone growth factor extracted in PBS (%) | 0 | 0 |
| Bone growth factor extracted in 100 mmol/l HCl (%) | 70.3 | 32.5 |
| Total Protein Recovery (%) | 70.3 | 32.5 |

There is a significant difference in coating of titan sheets with bone growth factor solutions with or without 10% sucrose. From the sample containing sucrose 32.5% of the protein is recovered, from the sample without sucrose 70.3% of bone growth factor are recovered (see FIG. 7).

In the experiments described above, we wanted to evaluate the presence of sucrose in coating solutions on binding of bone growth factor on metallic surfaces. The results demonstrate that the total recovery is significantly lower than the recovery of bone growth factor after coating without sucrose.

EXAMPLE 10

Coating and Release of Ti6Al4V Bone Growth Factor—Influence of Reducing Agents

A) Influence of Reducing Agents in the Coating Solution:

To avoid protein oxidation of the protein during the coating and extraction cycle, we included reducing agents in the coating solution: We added 10 mmol/l of the following compounds to the bone growth factor coating solution or a combination thereof:

10 µl Sample 1 (Blank): 5.04 mg/ml bone growth factor in 10 mmol/l HCl.

12 µl sample 2: 10 mmol/l EDTA+3.94 mg/ml bone growth factor

10 µl sample 3: 10 mmol/l Met+4.54 mg/ml bone growth factor

10 µl sample 4: 10 mmol/l $Na_2SO_3$+4.54 mg/ml bone growth factor

11 µl sample 5: 10 mmol/l Met+10 mmol/l EDTA+3.84 mg/ml bone growth factor

11 µl sample 6: 10 mmol/l EDTA+10 mmol/l $Na_2SO_3$+3.84 mg/ml bone growth factor; and performed the coating as described in example 5.

Extraction:

First bone growth factor was extracted with PBS for 1 h at room temperature (incubation in PBS represents a simulation of the physiological situation in the body). Subsequently, the sheets were extracted with 10 mmol/l HCl for 3 h. The bone growth factor in the extraction solutions of every sample was quantified by RP-HPLC as described in example 1. The amount of oxidized protein was determined as described in example 4. The results of the experiments described above are summarized in table 5:

The coating and the extraction procedure was performed at 4° C. and at room temperature. First rhGDF-5 was extracted with PBS for 1 h at room temperature. Then the sheets were incubated in 10 mmol/l HCl for 3 h. The rhGDF-5 in the extraction solutions of every sample were quantified by RP-HPLC (Example 1). Subsequently the amount of oxidized species was determined by RP-HPLC (Example 4).

In table 6 the samples are listed according their mode of pretreatment.

TABLE 5

| | Sample No | | | | | | |
|---|---|---|---|---|---|---|---|
| | 1 | 2 | 3 | 4 | 5 | 6 | 7 |
| Reducing agent | None (blank) | EDTA | Met | $Na_2SO_3$ | EDTA/ Met | EDTA/ $Na_2SO_3$ | Bulk |
| Bone growth factor extracted in PBS (%) | 13 | 78 | 41 | — | 53 | 50 | — |
| Extraction of bone growth factor in 10 mmol/l HCl (%) | 69 | — | 32 | 76 | — | — | — |
| Total Protein recovery | 82 | 78 | 73 | 76 | 53 | 50 | — |
| Amount of oxidized species after PBS extraction (%) | — | 13 | 8 | — | 9 | 14 | |
| Amount of oxidized species after HCl extraction | 10 | *) | 12 | 23 | *) | *) | 5 in HCl (no extraction) |

*) No protein was detected after HCl extraction by HPLC quantification

The recovery of all samples is between 50% and 82%. Protein is extracted in PBS in all samples except the one containing $Na_2SO_3$. The amount of oxidized species was determined in samples extracted in PBS as well as in samples extracted in HCl. The amount of oxidized species is between 8% and 23%.

In conclusion the method using reducing agents in the coating solution is not the method of choice to avoid oxidation of bone growth factor. Either the total recovery is low or the protein is already extracted in PBS to a great extent or the amount of oxidized bone growth factor is significantly high. Therefore other methods are necessary to avoid oxidation of bone growth factor during the coating and extraction cycle.

B) Soaking of the Surface with Reducing Agents Prior to the Start of the Coating Process:

We described the influence of reducing agents in the coating solution. Here we compare the effect of different reducing agents after incubating pretreated metal sheets for 24 h in a solution containing the respective reducing agent. Subsequently the coating and extraction procedure was performed at two different temperatures.

All samples were incubated in one of a 10 mmol/l solution of the following reducing agents: Thiocarbamide, ascorbic acid, sodium sulfite, cysteine, methionine, mercaptoethanol.

After incubation for 24 h the sheets were washed in demineralized water and dried for 15 min under vacuum at room temperature.

All sheets were laid down flat in a dish and coated with 10 μl of a 6.95 mg/ml rhGDF-5 solution on one side of the metal sheet. Half of the number of the sheets were dried under vacuum at 4° C., the other half of the sheets was dried under vacuum at room temperature.

TABLE 6

| Sample No. | Pretreatment II | Temperature of C/E | % oxidized rhGDF-5 |
|---|---|---|---|
| 1 | thiocarbamide | 4° C. | 12.2 |
| 2 | ascorbic acid | 4° C. | 12.6 |
| 3 | sodium sulfite | 4° C. | 9 |
| 4 | cysteine | 4° C. | 9.7 |
| 5 | methionine | 4° C. | 11.1 |
| 6 | mercaptoethanol | 4° C. | 11.3 |
| 7 | thiocarbamide | RT | 15.0 |
| 8 | ascorbic acid | RT | 15.1 |
| 9 | sodium sulfite | RT | 17.3 |
| 10 | cysteine | RT | 17.8 |
| 11 | methionine | RT | 16.1 |
| 12 | mercaptoethanol | RT | 14.7 |
| Bulk | None | RT | 5.0 |

The amount of oxidized rhGDF-5 in all samples is between 9.0% and 12.6%, while the protein solution used as starting material had a content of 5% oxidized species. In the samples incubated at 4° C. the amount of oxidized protein is lower than in the respective samples treated at room temperature. From the results it is concluded that none of the used excipients is able to significantly avoid oxidation. The amount of oxidized protein is displayed in FIGS. 8 and 9.

The main issue of the experiment described here is the incubation of the pretreated sheets with different reducing agents. We conclude that incubation of the metal sheets for 24 h in solutions of reducing agents is not the method of choice for avoidance of protein oxidation.

EXAMPLE 11

Quantification of rhproBMP-2 and rhBMP-2 by Means of RP-HPLC

The amount of rhproBMP-2/rhBMP-2 is determined by reversed phase HPLC analysis. The sample is applied to a Poros C4-column (20×2 mm) which has been equilibrated with 0.045% TFA. After washing of the column, the elution takes place with 0.025% TFA, 84% acetonitrile, and a gradient of 21-84% acetonitrile (flow: 0.4 ml/min). The elution is observed by measuring the absorbtion at 220 nm. The quantification takes place via the peak and use of a standard curve.

EXAMPLE 12

Determination of Chemical Modifications of the Extracted rhproBMP-2

The amount of modified forms of bone growth factor in solutions containing extracted protein was determined by RP-HPLC. The sample is applied to a YMC C4 column (4.6× 250 mm) which has been equilibrated with 0.1% TFA. After washing of the column, the elution takes place with a mixture of 100% acetonitril, 0.1% TFA, and a stepwise gradient of 25%-100% acetonitrile (flow: 0.8 ml/min). The elution is observed by measuring the absorbance at 220 nm. The relative amount of modified species is calculated from the ration of the respective peak area and the total peak area.

EXAMPLE 13

Determination of the Amount of Modified rhproBMP-2 after Extraction

In this example, the behavior of rhproBMP-2 during the coating-extraction process at optimized conditions was investigated: rhproBMP2 is the recombinant form of pro-BMP-2. The amino acid sequence of said rhproBMP2 is shown in SEQ ID NO: 4. After extraction the amount of modified species was determined.

Coating:

Titan sheets were coated with rhproBMP-2 as described in Example 5, supra. One set of sheets was coated at standard conditions (air, room temperature) (set 1); another set of sheets was coated under $N_2$ atmosphere (set 2).

Each sheet was laid down flat in a dish and coated with 10 µl of a 1,9 mg/ml rhproBMP-2 solution on one side of the metal sheet, respectively.

Extraction:

Extraction was performed as described in Example 5, supra. The amount of modified rhproBMP-2 was also determined by RP-HPLC; see Example 12, supra.

Characterization of the extracted protein was performed by the quantification of the modified species. Accordingly, the changes in the amount of modified rhproBMP-2 were compared to rhproBMP-2 bulk solution. These data are displayed in table 7 showing the amount of chemically modified rhproBMP-2 after extraction:

TABLE 7

| Sample No. | Atmosphere | % of modified protein compared to coating solution | MW | 1 × SD |
|---|---|---|---|---|
| 1 | air | 6.3 | 4.9 | 1.2 |
| 2 | air | 4.1 | | |
| 3 | air | 4.2 | | |
| 4 | N2 | 1.9 | 1.5 | 0.6 |
| 5 | N2 | 1.8 | | |
| 6 | N2 | 0.9 | | |
| Standard rhBMP-2 | Air | 0 | — | — |

The parameters tested in the experiments here have an influence on the amount of modified rhproBMP-2 after extraction from the titan sheets: Samples coated under air atmosphere reveal an amount of modified rhproBMP-2 of 4.9%±1.2% as compared to the coating solution displayed in table 2, supra.

The samples processed at room temperature and under $N_2$ gas show 1.5%±0.6% increase of modified rhproBMP-2 after extraction.

The samples treated under air reveal an increase of +4.9% (see FIG. 10, infra) as compared to the protein bulk solution. FIG. 10 shows the increase of modified rhproBMP-2 after coating/extraction compared to the coating solution. In FIG. 10, infra, the error bars of the respective samples are not overlapping. Therefore, it was concluded that the surrounding gas atmosphere has a significant influence on the amount of modifications of rhproBMP-2 after extraction from the titan sheets.

REFERENCES

Albrektsson T. in: Handbook of Biomaterials (Black, J and Hastings, G (eds.), Chapman & Hall, London, 1998, pp 500-512).

Endo, K. Dental Materials Journal 14(2): 185-198, 1995

Jennissen, H. et al., Biomaterialien (2001), 2, 45-53

Kim, H. et al., J Biomed Mater Res, 45, 100-107, 1999

Koeck, B. and Wagner, W. Implantologie, Urban & Schwarzenberg 1. Auflage, 1996.

Lichtinger, T. K. et al., Mat.-wiss. u. Werkstofftech, 32 (2001) 937-941

Shah, A. et al., Biology of the cell 91, 131-142 (1999)

Strnad, Z. et al., Int J Oral Maxillofac Implants 2000; 15:483-490

Tsui, Y. et al., Biomaterials, 19 (1998) 2031-2043

Voggenreiter G, Hartl H, Assenmacher S, Chatzinikolaidou M, Rumpf H M, Jennissen H P. (2001), Assessment of the Biological Activity of Chemically Immobilized rhBMP-2 on Titanium surfaces in vivo *Materialwiss.Werkstofftech.* 32, 942-948

Wen, H. et al, Journal of Material Science: Materials in Medicine 9 (1998) 121-128

Williams, D. F. Proceedings of a Consensus Conference of the European Society for Biomaterials (ESB) Elsevier, Amsterdam, p. 60.

Williams, D. F. The Williams Dictionary of Biomaterials (Liverpool, UK: Liverpool University Press (1999) 40.

The invention claimed is:

1. A method for the production of a device comprising the steps of:
   (a) providing a solution comprising dissolved osteoinductive protein, wherein the solution allows the dissolution of the protein for a time sufficient for homogenous coating;
   (b) contacting the solution of step (a) with a carrier containing a surface of metal or a metal alloy;
   (c) allowing coating of the surface of said carrier with said dissolved protein, wherein the carrier is entirely coated with the protein so that identical amounts of the protein are present in each and every area of the surface of the carrier, thereby resulting in a homogenously coated carrier; and
   (d) drying of the coated carrier obtained in step (c), wherein steps (b) to (d) are carried out under a reduced concentration of oxygen.

2. The method of claim 1, wherein steps (b) to (d) are carried out under an oxygen concentration of less than 10 vol % oxygen.

3. The method of claim 1, wherein steps (b) to (d) are carried out at a temperature below 25° C.

4. The method of claim 1, wherein said metal or metal alloy is titanium or a titanium alloy.

5. The method of claim 4, wherein the titanium alloy is a titanium alloy containing at least 50% titanium.

6. The method of claim 4, wherein the titanium alloy is a Ti—Al—V-alloy, a Ti—Al—Fe alloy, a Ti—Al—Nb-alloy or a Ti—Mo—Zr—Al-alloy.

7. The method of claim 6, wherein the Ti—Al—V-alloy is Ti6Al4V.

8. The method of any one of claims 1 to 7, wherein the coating is carried out by dipping the metallic surface into said protein solution.

9. The method of any one of claims 1 to 7, wherein the coating is carried out by dropping said protein solution onto the metallic surface.

10. The method of any one of claims 1 to 7, wherein the coating is carried out by spraying said protein solution onto the metallic surface.

11. The method of any one of claims 1 to 7, wherein the drying is achieved by vacuum drying.

12. The method of any one of claims 1 to 7, wherein the drying is achieved by freeze drying.

13. The method of any one of claims 1 to 7, wherein the drying is achieved by evaporation at room temperature in an inert gas stream.

14. The method of any one of claims 1 to 7, wherein said osteoinductive protein is a member of the TGF-β family.

15. The method of claim 14, wherein said member of the TGF-β family is a member of the BMP subfamily.

16. The method of claim 15, wherein said member of the BMP family is BMP2 or BMP7.

17. The method of claim 14, wherein said member of the TGF-β family is a member of the GDF subfamily.

18. The method of claim 17, wherein said member of the GDF subfamily is GDF-5.

19. The method of any one of claims 1 to 7, wherein said device is free of toxic substances.

20. The method of any one of claims 1 to 7, wherein said solution allows the dissolution of said protein for a time sufficient for homogenous coating of said metallic surface of the carrier.

21. The method of any one of claims 1 to 7, wherein said solution allows a concentration of said osteoinductive protein of more than 0.5 mg/ml.

22. The method of claim 21, wherein said solution has an acidic pH.

23. The method of claim 22, wherein said acidic solution contains HCl, acetic acid, citric acid or succinic acid.

24. The method of claim 22, wherein the concentration of the acid is less than or equal to 100 mmol/l.

25. The method of any one of claims 1 to 7, wherein the solution is saturated with an inert gas.

26. The method of claim 25, wherein the inert gas is nitrogen, argon or helium.

27. The method of any one of claims 1 to 7, which is carried out in a compartment with a controlled atmosphere and humidity.

* * * * *

SEQUENCE LISTING

<160> NUMBER OF SEQ ID NOS: 6

<210> SEQ ID NO 1
<211> LENGTH: 396
<212> TYPE: PRT
<213> ORGANISM: Homo sapiens

<400> SEQUENCE: 1

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
```

-continued

```
              355                 360                 365
Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 2
<211> LENGTH: 431
<212> TYPE: PRT
<213> ORGANISM: Homo Sapiens

<400> SEQUENCE: 2

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335
```

```
Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
            370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 3
<211> LENGTH: 501
<212> TYPE: PRT
<213> ORGANISM: Homo Sapiens

<400> SEQUENCE: 3

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
            20                  25                  30

Gln Arg Pro Gln Gly Ser Arg Pro Gly Leu Ala Lys Ala Glu Ala Lys
            35                  40                  45

Glu Arg Pro Pro Leu Ala Arg Asn Val Phe Arg Pro Gly Gly His Ser
        50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
            115                 120                 125

Pro Gly Gly Lys Ala Pro Pro Lys Ala Gly Ser Val Pro Ser Ser Phe
        130                 135                 140

Leu Leu Lys Lys Ala Arg Glu Pro Gly Pro Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
            195                 200                 205

Gly Gln Asp Asp Arg Gly Pro Val Val Arg Lys Gln Arg Tyr Val Phe
        210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Val Pro Arg
                245                 250                 255

Ser Arg Arg Ala Ala Gln Leu Lys Leu Ser Ser Cys Pro Ser Gly Arg
            260                 265                 270

Gln Pro Ala Ala Leu Leu Asp Val Arg Ser Val Pro Gly Leu Asp Gly
            275                 280                 285
```

```
Ser Gly Trp Glu Val Phe Asp Ile Trp Lys Leu Phe Arg Asn Phe Lys
    290                 295                 300

Asn Ser Ala Gln Leu Cys Leu Glu Leu Glu Ala Trp Glu Arg Gly Arg
305                 310                 315                 320

Thr Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Arg Asp
        340                 345                 350

Leu Phe Phe Asn Glu Ile Lys Ala Arg Ser Gly Gln Asp Asp Lys Thr
            355                 360                 365

Val Tyr Glu Tyr Leu Phe Ser Gln Arg Arg Lys Arg Ala Pro Leu
    370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
        435                 440                 445

Ile Gln Thr Leu Met Asn Ser Met Asp Pro Ser Thr Pro Pro Thr
    450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500

<210> SEQ ID NO 4
<211> LENGTH: 373
<212> TYPE: PRT
<213> ORGANISM: Homo Sapiens

<400> SEQUENCE: 4

Leu Val Pro Glu Leu Gly Arg Arg Lys Phe Ala Ala Ala Ser Ser Gly
1               5                   10                  15

Arg Pro Ser Ser Gln Pro Ser Asp Glu Val Leu Ser Glu Phe Glu Leu
            20                  25                  30

Arg Leu Leu Ser Met Phe Gly Leu Lys Gln Arg Pro Thr Pro Ser Arg
        35                  40                  45

Asp Ala Val Val Pro Pro Tyr Met Leu Asp Leu Tyr Arg His Ser
    50                  55                  60

Gly Gln Pro Gly Ser Pro Ala Pro Asp His Arg Leu Glu Arg Ala Ala
65                  70                  75                  80

Ser Arg Ala Asn Thr Val Arg Ser Phe His His Glu Glu Ser Leu Glu
                85                  90                  95

Glu Leu Pro Glu Thr Ser Gly Lys Thr Thr Arg Arg Phe Phe Phe Asn
            100                 105                 110

Leu Ser Ser Ile Pro Thr Glu Glu Phe Ile Thr Ser Ala Glu Leu Gln
        115                 120                 125

Val Phe Arg Glu Gln Met Gln Asp Ala Leu Gly Asn Asn Ser Ser Phe
    130                 135                 140

His His Arg Ile Asn Ile Tyr Glu Ile Ile Lys Pro Ala Thr Ala Asn
```

```
                145                 150                 155                 160
Ser Lys Phe Pro Val Thr Arg Leu Leu Asp Thr Arg Leu Val Asn Gln
                165                 170                 175

Asn Ala Ser Arg Trp Glu Ser Phe Asp Val Thr Pro Ala Val Met Arg
            180                 185                 190

Trp Thr Ala Gln Gly His Ala Asn His Gly Phe Val Val Glu Val Ala
            195                 200                 205

His Leu Glu Glu Lys Gln Gly Val Ser Lys Arg His Val Arg Ile Ser
        210                 215                 220

Arg Ser Leu His Gln Asp Glu His Ser Trp Ser Gln Ile Arg Pro Leu
225                 230                 235                 240

Leu Val Thr Phe Gly His Asp Gly Lys Gly His Pro Leu His Lys Arg
                245                 250                 255

Glu Lys Arg Gln Ala Lys His Lys Gln Arg Lys Arg Leu Lys Ser Ser
            260                 265                 270

Cys Lys Arg His Pro Leu Tyr Val Asp Phe Ser Asp Val Gly Trp Asn
            275                 280                 285

Asp Trp Ile Val Ala Pro Pro Gly Tyr His Ala Phe Tyr Cys His Gly
        290                 295                 300

Glu Cys Pro Phe Pro Leu Ala Asp His Leu Asn Ser Thr Asn His Ala
305                 310                 315                 320

Ile Val Gln Thr Leu Val Asn Ser Val Asn Ser Lys Ile Pro Lys Ala
                325                 330                 335

Cys Cys Val Pro Thr Glu Leu Ser Ala Ile Ser Met Leu Tyr Leu Asp
            340                 345                 350

Glu Asn Glu Lys Val Val Leu Lys Asn Tyr Gln Asp Met Val Val Glu
            355                 360                 365

Gly Cys Gly Cys Arg
        370

<210> SEQ ID NO 5
<211> LENGTH: 398
<212> TYPE: PRT
<213> ORGANISM: Homo Sapiens

<400> SEQUENCE: 5

Met Gly Ser Ser His His His His His His Ser Ser Gly Leu Val Pro
1               5                   10                  15

Arg Gly Ser His Met Gly Ala Ala Gly Leu Val Pro Glu Leu Gly Arg
            20                  25                  30

Arg Lys Phe Ala Ala Ala Ser Ser Gly Arg Pro Ser Ser Gln Pro Ser
        35                  40                  45

Asp Glu Val Leu Ser Glu Phe Glu Leu Arg Leu Leu Ser Met Phe Gly
    50                  55                  60

Leu Lys Gln Arg Pro Thr Pro Ser Arg Asp Ala Val Val Pro Pro Tyr
65                  70                  75                  80

Met Leu Asp Leu Tyr Arg Arg His Ser Gly Gln Pro Gly Ser Pro Ala
                85                  90                  95

Pro Asp His Arg Leu Glu Arg Ala Ala Ser Arg Ala Asn Thr Val Arg
            100                 105                 110

Ser Phe His His Glu Glu Ser Leu Glu Glu Leu Pro Thr Ser Gly
        115                 120                 125

Lys Thr Thr Arg Arg Phe Phe Phe Asn Leu Ser Ser Ile Pro Thr Glu
    130                 135                 140
```

-continued

```
Glu Phe Ile Thr Ser Ala Glu Leu Gln Val Phe Arg Glu Gln Met Gln
145                 150                 155                 160

Asp Ala Leu Gly Asn Asn Ser Phe His His Arg Ile Asn Ile Tyr
            165                 170                 175

Glu Ile Ile Lys Pro Ala Thr Ala Asn Ser Lys Phe Pro Val Thr Arg
            180                 185                 190

Leu Leu Asp Thr Arg Leu Val Asn Gln Asn Ala Ser Arg Trp Glu Ser
            195                 200                 205

Phe Asp Val Thr Pro Ala Val Met Arg Trp Thr Ala Gln Gly His Ala
210                 215                 220

Asn His Gly Phe Val Val Glu Val Ala His Leu Glu Glu Lys Gln Gly
225                 230                 235                 240

Val Ser Lys Arg His Val Arg Ile Ser Arg Ser Leu His Gln Asp Glu
                245                 250                 255

His Ser Trp Ser Gln Ile Arg Pro Leu Leu Val Thr Phe Gly His Asp
                260                 265                 270

Gly Lys Gly His Pro Leu His Lys Arg Glu Lys Arg Gln Ala Lys His
            275                 280                 285

Lys Gln Arg Lys Arg Leu Lys Ser Ser Cys Lys Arg His Pro Leu Tyr
290                 295                 300

Val Asp Phe Ser Asp Val Gly Trp Asn Asp Trp Ile Val Ala Pro Pro
305                 310                 315                 320

Gly Tyr His Ala Phe Tyr Cys His Gly Glu Cys Pro Phe Pro Leu Ala
                325                 330                 335

Asp His Leu Asn Ser Thr Asn His Ala Ile Val Gln Thr Leu Val Asn
            340                 345                 350

Ser Val Asn Ser Lys Ile Pro Lys Ala Cys Cys Val Pro Thr Glu Leu
            355                 360                 365

Ser Ala Ile Ser Met Leu Tyr Leu Asp Glu Asn Glu Lys Val Val Leu
370                 375                 380

Lys Asn Tyr Gln Asp Met Val Val Glu Gly Cys Gly Cys Arg
385                 390                 395
```

<210> SEQ ID NO 6
<211> LENGTH: 501
<212> TYPE: PRT
<213> ORGANISM: Homo Sapiens

<400> SEQUENCE: 6

```
Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
            20                  25                  30

Gln Arg Pro Gln Gly Thr Arg Pro Gly Leu Ala Lys Ala Glu Ala Lys
        35                  40                  45

Glu Arg Pro Pro Leu Ala Arg Asn Val Phe Arg Pro Gly Gly His Ser
50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125
```

-continued

```
Pro Gly Gly Lys Ala Pro Pro Lys Ala Gly Ser Val Pro Ser Ser Phe
    130                 135                 140
Leu Leu Lys Lys Ala Arg Glu Pro Gly Pro Pro Arg Glu Pro Lys Glu
145                 150                 155                 160
Pro Phe Arg Pro Pro Ile Thr Pro His Glu Tyr Met Leu Ser Leu
                165                 170                 175
Tyr Arg Thr Leu Ser Asp Ala Asp Arg Lys Gly Gly Asn Ser Ser Val
                180                 185                 190
Lys Leu Glu Ala Gly Leu Ala Asn Thr Ile Thr Ser Phe Ile Asp Lys
                195                 200                 205
Gly Gln Asp Asp Arg Gly Pro Val Val Arg Lys Gln Arg Tyr Val Phe
    210                 215                 220
Asp Ile Ser Ala Leu Glu Lys Asp Gly Leu Leu Gly Ala Glu Leu Arg
225                 230                 235                 240
Ile Leu Arg Lys Lys Pro Ser Asp Thr Ala Lys Pro Ala Ala Pro Gly
                245                 250                 255
Gly Gly Arg Ala Ala Gln Leu Lys Leu Ser Ser Cys Pro Ser Gly Arg
                260                 265                 270
Gln Pro Ala Ser Leu Leu Asp Val Arg Ser Val Pro Gly Leu Asp Gly
    275                 280                 285
Ser Gly Trp Glu Val Phe Asp Ile Trp Lys Leu Phe Arg Asn Phe Lys
    290                 295                 300
Asn Ser Ala Gln Leu Cys Leu Glu Leu Glu Ala Trp Glu Arg Gly Arg
305                 310                 315                 320
Ala Val Asp Leu Arg Gly Leu Gly Phe Asp Arg Ala Ala Arg Gln Val
                325                 330                 335
His Glu Lys Ala Leu Phe Leu Val Phe Gly Arg Thr Lys Lys Arg Asp
                340                 345                 350
Leu Phe Phe Asn Glu Ile Lys Ala Arg Ser Gly Gln Asp Asp Lys Thr
                355                 360                 365
Val Tyr Glu Tyr Leu Phe Ser Gln Arg Arg Lys Arg Arg Ala Pro Leu
    370                 375                 380
Ala Thr Arg Gln Gly Lys Arg Pro Ser Lys Asn Leu Lys Ala Arg Cys
385                 390                 395                 400
Ser Arg Lys Ala Leu His Val Asn Phe Lys Asp Met Gly Trp Asp Asp
                405                 410                 415
Trp Ile Ile Ala Pro Leu Glu Tyr Glu Ala Phe His Cys Glu Gly Leu
                420                 425                 430
Cys Glu Phe Pro Leu Arg Ser His Leu Glu Pro Thr Asn His Ala Val
                435                 440                 445
Ile Gln Thr Leu Met Asn Ser Met Asp Pro Glu Ser Thr Pro Pro Thr
    450                 455                 460
Cys Cys Val Pro Thr Arg Leu Ser Pro Ile Ser Ile Leu Phe Ile Asp
465                 470                 475                 480
Ser Ala Asn Asn Val Val Tyr Lys Gln Tyr Glu Asp Met Val Val Glu
                485                 490                 495
Ser Cys Gly Cys Arg
    500
```